United States Patent [19]

Fraley et al.

[11] Patent Number: 5,352,605
[45] Date of Patent: Oct. 4, 1994

[54] CHIMERIC GENES FOR TRANSFORMING PLANT CELLS USING VIRAL PROMOTERS

[75] Inventors: Robert T. Fraley, Ballwin; Robert B. Horsch; Stephen G. Rogers, both of St. Louis, all of Mo.

[73] Assignee: Monsanto Company, St. Louis, Mo.

[21] Appl. No.: 146,621

[22] Filed: Oct. 28, 1993

Related U.S. Application Data

[63] Continuation of Ser. No. 625,637, Dec. 7, 1990, abandoned, which is a continuation of Ser. No. 931,492, Nov. 17, 1986, abandoned, which is a continuation-in-part of Ser. No. 485,568, Apr. 15, 1983, abandoned, which is a continuation-in-part of Ser. No. 458,414, Jan. 17, 1983, abandoned.

[51] Int. Cl.$^5$ .................. C12N 5/00; C12N 15/00; C07H 21/04
[52] U.S. Cl. .................. 435/240.4; 435/172.3; 435/320.1; 536/23.2; 536/24.1
[58] Field of Search .................. 536/23.2, 24.1; 435/172.3, 240.4, 320.1; 800/205

[56] References Cited

U.S. PATENT DOCUMENTS

| | | | |
|---|---|---|---|
| 4,536,475 | 8/1985 | Anderson | 435/172.3 |
| 5,034,322 | 7/1991 | Rogers et al. | 435/172.3 |

FOREIGN PATENT DOCUMENTS

| | | | |
|---|---|---|---|
| 0116718B1 | 5/1990 | European Pat. Off. | C12N 15/00 |
| 0116718 | 5/1990 | European Pat. Off. | C12N 15/00 |
| 0131623 | 3/1991 | European Pat. Off. | C12N 15/11 |
| 0142924 | 4/1992 | European Pat. Off. | C12N 15/05 |
| WO82/03087 | 9/1982 | PCT Int'l Appl. | C12N 15/00 |

OTHER PUBLICATIONS

Guilley et al. 1982. Cell 30(3): 763–773.
Zambryski et al. 1983. EMBO J 2(12): 2143–2150.
Goodman et al. 1987. Science 236: 48–54.
Ursic et al., *Biochemical and Biophysical Research Communications*, 101, 3, pp. 1031–1037 (1981).
Beck et al., *Gene*, 19, pp. 327–336 (1982).
Herrera-Estrela et al., *EMBO*, 6 pp. 987–995 (1983).
Maliga et al., *Molec. Gen. Genet.*, 157, pp. 291–296 (1977).
De Greve et al., *Nature*, 30, pp. 752–755 (1982).
Portetelle et al., *Annales De Gemblous*, 87, 3, pp. 101–123 (1981).
Larkins et al. 1985. J. Cell. Biochem. Suppl. 9C:264.
Barton et al. 1987. Plant Physiol. 85:1103–1109.
Berry-Lowe et al., J. Mol. & Appl. Gent., 1(6): 483–498 (1982).
Bevan et al., Nature, 304: 184–187 (1983).
Cairns et al., Febs Letters, 96(2): 295–297 (1978).
Cairns et al., PNAS, 75(11): 5557–5559 (1978).
Chilton et al., PNAS, 77: 4060–4064 (1977).
Chilton et al., Stadler Symp., 13:39–51 (1981).
Chilton et al., Nature, 295: 432–434 (1982).
Chilton et al., The Fifteenth Miami Winter Symposium, 17–21 Jan. 1983, 14–15, Ahmad et al., (1983).
Colbere-Gerapin et al, J. Mol. Biol., 150: 1–14 (1981).
Condit et al., Miami Winter Symposium, Jan. 17–21, p. 564 (1983).
Davey et al., Transformation in plants: potential and reality—Conference paper from University of Nottingham (1982).

(List continued on next page.)

*Primary Examiner*—David T. Fox
*Attorney, Agent, or Firm*—Lawrence M. Lavin, Jr.; Dennis R. Hoerner, Jr.; Howard C. Stanley

[57] ABSTRACT

In one aspect the present invention relates to the use of viral promoters in the expression of chimeric genes in plant cells. In another aspect this invention relates to chimeric genes which are capable of being expressed in plant cells, which utilize promoter regions derived from viruses which are capable of infecting plant cells. One such virus comprises the cauliflower mosaic virus (CaMV). Two different promoter regions have been derived from the CaMV genome and ligated to heterologous coding sequences to form chimeric genes. These chimeric genes have been shown to be expressed in plant cells. This invention also relates to plant cells, plant tissue, and differentiated plants which contain and express the chimeric genes of this invention.

19 Claims, 10 Drawing Sheets

OTHER PUBLICATIONS

DeGreve et al., J. Mol. Appl. Genet., 1(6): 499–511 (1983).
Depicker et al., J. Mol. & Appl. Genet. 1(6): 561–573 (1982).
Depicker et al., Conference Paper, Davis, pp. 143–176 (1982).
Dix et al., Molec. Gen. Genet., 157: 285–290 (1977).
Fraley et al., PNAS, 80: 4803–4807 (1983).
Fraley et al., Miami Winter Symposia, Advances in Gene Technology: Molecular Genetics of Plants and Animals, 20: 211–221 (1983).
Franck et al., Cell, 21: 285–294 (1980).
Gardner, "Genetic Engineering of Plants–An Agricultural Perspective", Kosuge et al., (eds) pp. 121–142 (1982).
Garfinkel et al., Cell, 27:143–153 (1981).
Groneborn et al., Nature, 294: 773–776 (1981).
Hernalsteens et al., Nature, 287: 654–656 (1980).
Herrera-Estrella et al., Nature, 303: 209–213 (1983).
Hohn et al., "Current Topics in Microbiology and Immunology" Henle et al. (eds) vol. 96, pp. 193–236 (1982).
Holsters et al., Mol Gen Genet, 185: 283–290 (1982).
Howell et al., Science, 208: 1265–1267 (1980).
Jimenez et al., Nature, 287: 869–871 (1980).
Kemp et al., Genetic Engineering–Application to Agriculture, pp. 215–228, (1983).
Lebeurier et al., Gene, 12: 139–146 (1980).
Leemans, Universite Libre de Bruxelles, Thesis, 1–25; 114–125 (1982).
Leemans et al., J. Mol. & Appl. Genet. 1(2): 149–164 (1981).
Leemans et al., EMBO, 1(1): 147–152 (1982).
Leemans et al., "Molecular Biology of Plant Tumors" Chap. 21, pp. 537–545 (1982).
Liu et al., PNAS, 79: 2812–2816 (1982).
McKnight et al., J. of Virology, 37(2): 673–682 (1981).
Matzke et al., J. Mol. & Appl. Genet., 1: 39–49 (1981).
Meagher et al., "Genome Organization and Expression in Plants" Leaver, C. J. (ed), NATO Advance Study Institute Series, 29: 63–75 (1980).
Mulligan et al., Nature, 277: 108–114 (1979).
Mulligan et al., Science, 209: 1422–1427 (1980).
Mulligan et al., PNAS, 75(4): 2072–2076 (1981).
O'Hare et al., PNAS 78(3): 1527–1531 (1981).
Old et al., "Principles of Gene Manipulation", U. of Calif. Press, 1st ed. vol. 2 pp. 9–23 (1980).
Old et al., "Principles of Gene Manipulation", U. of Calif. Press, 2nd Ed., vol. 2 pp. 121–210 (1980).
Olszewski et al., Cell, 29: 395–402 (1982).
Otten et al., Mol Gen Genet, 183: 209–213 (1981).
Schell et al., abstract from "Broadening the Genetic Base of Crops", Harten et al. (eds) (1978).
Schell et al., abstract from "Plant Improvement and Somatic Cell Genetics" Vasil et al., (eds) (1982).
Schell et al., Biotechnology, 175–180 (1983).
Schell et al., The Fifteenth Miami Winter Symposium, 17–21 Jan. 1983, pp. 191–209. (1983).
Schroeder at al., "Plant Cell Culture in Crop Improvement", Sen et al., (eds) pp. 287–297 (1983).
Watson, "Molecular Biology of the Gene" 3rd ed., W. A. Benjamin, Inc. (publisher), pp. 482–483 (1977).
Willmitzer et al., Nature, 287: 359–361 (1980).
Wilmitzer et al., EMBO, 1(1): 139–146 (1982).
Colbere-Garapin et al., "A New Dominant Hybrid Selective Marker for Higher Eukaryotic Cells," *J. Mol. Biol.* (1981) vol. 150, pp. 1–14.
Guilley et al., "Transcription of Cauliflower Mosaic Virus DNA: Detection of Promoter Sequences, and Characterization of Transcripts," *Cell* (1982) vol. 30, pp. 763–773.
Condit et al., Miami Winter Symposiumm Jan. 17–21, 1983, Abstract: "Multiple Viral Specific Transcripts from the Genome of Cauliflower Mosaic Virus".
Howell et al., "Cloned Cauliflower Mosaic Virus DNA Infects Turnips (*Brassica rapa*)" (1980) *Science,* vol. 208, pp. 1265–1267.
McKnight et al., "Isolation and Mapping of Small Cauliflower Mosaic Virus DNA Fragments Active as Promoters in *Escherichia coli*" (1981) *Journal of Virology* vol. 37, No. 2, pp. 673–682 (Abstract Only).
Gardner, R. C., "Plant Viral Vectors: CaMV as an Experimental Tool," Genetic Engineering of Plants, an Agricultural Perspective, Proceedings of a Symposium held Aug. 15–19, 1982 at the University of California, Davis, Calif., Kusuge et al., Ed., pp. 124–125, 128 and 138.
Leemans et al., "Ti Plasmids and Directed Genetic Engineering" (1982) *Molecular Biology of Plant Tumors,* pp. 537–545.
Hohn et al, "Cauliflower Mosaic Virus on Its Way to Becoming a Useful Plant Vector" (1982) *Current Topics in Microbiology and Immunology* vol. 96, pp. 193–236.
Lebeurier et al, "Infectivities of Native and Cloned DNA of Cauliflower Mosaic Virus" (1980) *Gene,* vol. 12, pp. 139–146.
Davey et al., Conference paper from University of Nottingham (1982) Derwent Abstract 028990, DBA Accession No: 84–12265.

CHIMERIC GENES FOR TRANSFORMING PLANT CELLS USING VIRAL PROMOTERS

RELATED APPLICATIONS

This is a File Wrapper continuation of application Ser. No. 07/625,637, filed Dec. 7, 1990, now abandoned, which is a continuation of U.S. Ser. No. 06/931,492, filed Nov. 17, 1986, now abandoned, which is a continuation-in-part of U.S. Ser. No. 06/485,568, filed Apr. 15, 1983, now abandoned, which is a continuation-in-part of U.S. Ser. No. 06/458,414, filed Jan. 17, 1983, now abandoned.

TECHNICAL FIELD

This invention is in the fields of genetic engineering and plant biology.

BACKGROUND ART

A virus is a microorganism comprising single or double stranded nucleic acid (DNA or RMA) contained within a protein (and possibly lipid) shell called a "capsid" or "coat". A virus is smaller than a cell, and it does not contain most of the components and substances necessary to conduct most biochemical processes. Instead, a virus infects a cell and uses the cellular processes to reproduce itself.

The following is a simplified description of how a DNA-containing virus infects a cell; RNA viruses will be disregarded in this introduction for the sake of clarity. First, a virus attaches to or enters a cell, normally called a "host" cell. The DNA from the virus (and possibly the entire viral particle) enters the host cell where it usually operates as a plasmid (a loop of extra-chromosomal DNA). The viral DNA is transcribed into messenger RNA, which is translated into one or more polypeptides. Some of these polypeptides are assembled into new capsids, while others act as enzymes to catalyze various biochemical reactions. The viral DNA is also replicated and assembled with the capsid polypeptides to form new viral particles. These viral particles may be released gradually by the host cell, or they may cause the host cell to lyse and release them. The released viral particles subsequently infect new host cells. For more background information on viruses see, e.g., Stryer, 1981 and Matthews, 1970 (note: all references cited herein, other than patents, are listed with citations after the examples).

As used herein, the term "virus" includes phages and viroids, as well as replicative intermediates. As used herein, the phrases "viral nucleic acid" and DNA or RNA derived from a virus" are construed broadly to include any DNA or RNA that is obtained or derived from the nucleic acid of a virus. For example, a DNA strand created by using a viral RNA strand as a template, or by chemical synthesis to create a known sequence of bases determined by analyzing viral DNA, would be regarded as viral nucleic acid.

The host range of any virus (i.e., the variety of cells that a type of virus is capable of infecting) is limited. Some viruses are capable of efficient infection of only certain types of bacteria; other viruses can infect only plants, and may be limited to certain genera; some viruses can infect only mammalian cells. Viral infection of a cell requires more than mere entry of the viral DNA or RNA into the host cell; viral particles must be reproduced within the cell. Through various assays, those skilled in the art can readily determine whether any particular type of virus is capable of infecting any particular genus, species, or strain of cells. As used herein, the term "plant virus" is used to designate a virus which is capable of infecting one or more types of plant cells, regardless of whether it can infect other types of cells.

With the possible exception of viroids (which are poorly understood at present), every viral particle must contain at least one gene which can be "expressed" in infected host cells. The expression of a gene requires that a segment of DNA or RNA must be transcribed into or function as a strand of messenger RNA (mRNA), and the mRNA must be translated into a polypeptide. Most viruses have about 5 to 10 different genes, all of which are expressed in a suitable host cell.

In order to be expressed in a cell, a gene must have a promoter which is recognized by certain enzymes in the cell. Gene promoters are discussed in some detail in the parent application Ser. No. 458,414 cited above, the contents of which are incorporated herein by reference. Those skilled in the art recognize that the expression of a particular gene to yield a polypeptide is dependent upon two distinct cellular processes. A region of the 5' end of the gene called the promoter, initiates transcription of the gene to produce a mRNA transcript. The mRNA is then translated at the ribosomes of the cell to yield an encoded polypeptide. Therefore, it is evident that although the promoter may function properly, ultimate expression of the polypeptide depends at least in part on post-transcriptional processing of the mRNA transcript.

Promoters from viral genes have been utilized in a variety of genetic engineering applications. For example, chimeric genes have been constructed using various structural sequences (also called coding sequences) taken from bacterial genes, coupled to promoters taken from viruses which can infect mammalian cell(the most commonly used mammalian viruses are designated as Simian Virus 40 (SV40) and Herpes Simplex Virus (HSV)). These chimeric genes have been used to transform mammalian cells. See, e.g., Mulligan et al 1979; Southern and Berg 1982. In addition, chimeric genes using promoters taken from viruses which can infect bacterial cells have been used to transform bacterial cells; see, e.g., the phage lambda $P_L$ promoter discussed in Maniatis et al, 1982.

Several researchers have theorized that it might be possible to utilize plant viruses as vectors for transforming plant cells. See, e.g., Hohn et al, 1982. In general, a "vector" is a DNA molecule useful for transferring one or more genes into a cell. Usually, a desired gene is inserted into a vector, and the vector is then used to infect the host cell.

Several researchers have theorized that it might be possible to create chimeric genes which are capable of being expressed in plant cells, by using promoters derived from plant virus genes. See, e.g., Hohn et al, 1982, at page 216.

However, despite the efforts of numerous research teams, prior to this invention no one had succeeded in (1) creating a chimeric gene comprising a plant virus promoter coupled to a heterologous structural sequence and (2) demonstrating the expression of such a gene in any type of plant cell.

CAULIFLOWER MOSAIC VIRUS (CaMV)

The entire DNA sequence of CaMV has been published. Gardner et al, 1981; Hohn et al, 1982. In its most common form, the CaMV genome is about 8000 bp long. However, various naturally occurring infective mutants which have deleted about 500 bp have been discovered; see Howarth et al 1981. The entire CaMV genome is transcribed into a single mRNA, termed the "full-length transcript" having a sedimentation coefficient of about 35S. The promoter for the full-length mRNA (hereinafter referred to as "CaMV(35S)") is located in the large intergenic region about 1 kb counterclockwise from Gap 1 (see Guilley et al, 1982).

CaMV is believed to generate at least eight proteins; the corresponding genes are designated as Genes I through VIII. Gene VI is transcribed into mRNA with a sedimentation coefficient of 19S. The 19S mRNA is translated into a protein designated as P66, which is an inclusion body protein. The 19S mRNA is promoted by the 19S promoter, located about 2.5 kb counterclockwise from Gap 1.

SUMMARY OF THE INVENTION

In one aspect, the present invention relates to the use of viral promoters in the expression of chimeric genes in plant cells. In another aspect this invention relates to chimeric genes which are capable of being expressed in plant cells, which utilize promoter regions derived from viruses which are capable of infecting plant cells. One such virus comprises the cauliflower mosaic virus (CaMV). Two different promoter regions have been derived from the CaMV genome and ligated to heterologous coding sequences to form chimeric genes. These chimeric genes have been proven to be expressed in plant cells. This invention also relates to plant cells, plant tissue (including seeds and propagules), and differentiated plants which have been transformed to contain viral promoters and express the chimeric genes of this invention, and to polypeptides that are generated in plant cells by the chimeric genes of this invention.

BRIEF DESCRIPTION OF THE DRAWINGS

The figures herein are schematic representations; they have not been drawn to scale.

DETAILED DESCRIPTION OF THE INVENTION

Figure 1:
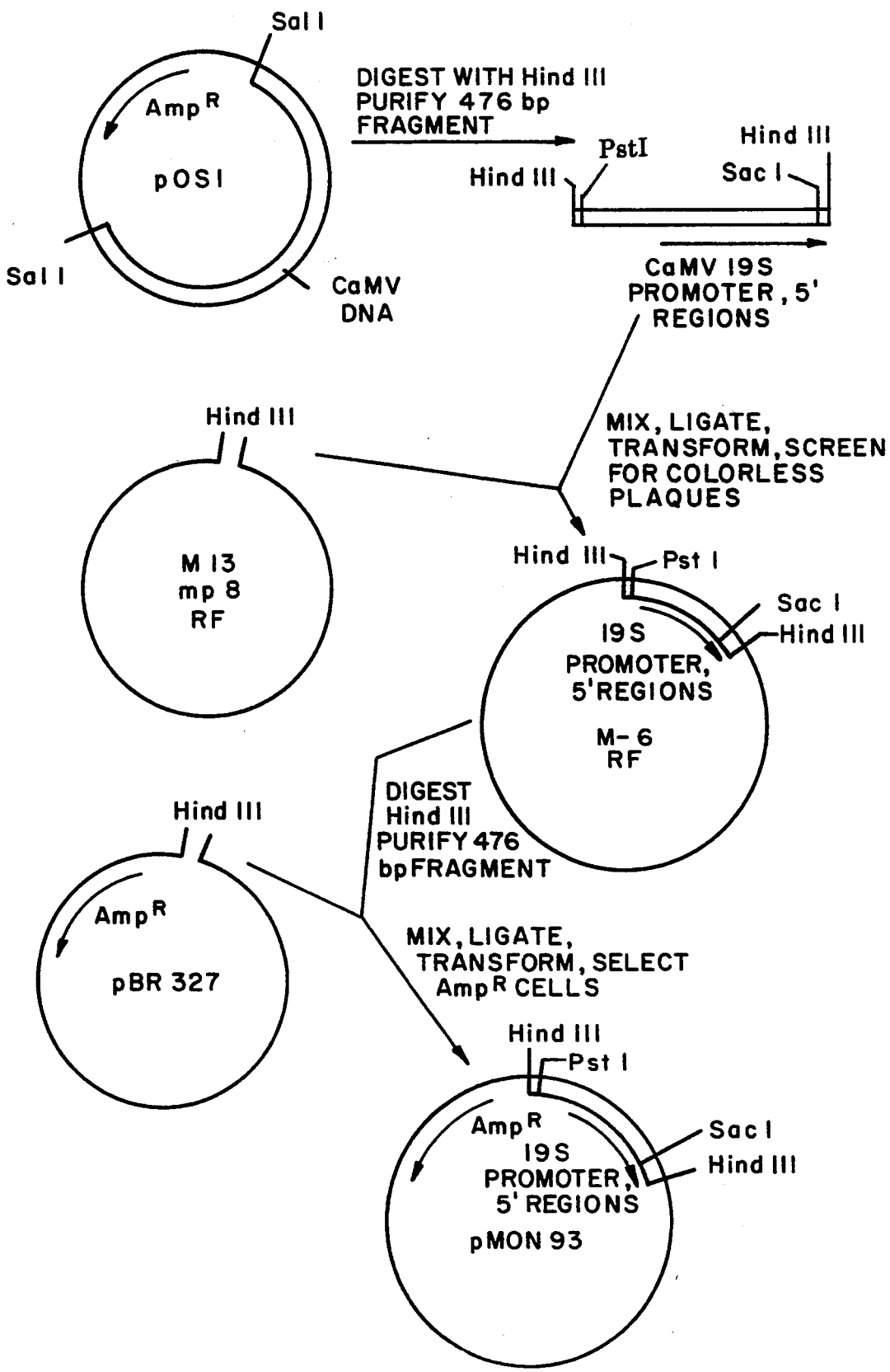
FIG. 1 represents the creation and structure of plasmid pMON93.

In one preferred embodiment of this invention, a chimeric gene was created which contained the following elements:

1. a promoter region and a 5' non-translated region derived from the CaMV (19S) gene, which codes for the P66 protein;
2. a partial coding sequence from the CaMV (19S) gene, including an ATG start codon and several internal ATG sequences, all of which were in the same frame as a TGA termination sequence immediately inside the desired ATG start codon of the NPTII gene;
3. a structural sequence derived from a neomycin phosphotransferase II (NPTII) gene; this sequence was preceded by a spurious ATG sequence, which was in the same reading frame as a TGA sequence within the NPTII structural sequence; and,
4. a 3' non-translated region, including a poly-adenylation signal, derived from a nopaline synthase (NOS) gene.

This chimeric gene, referred to herein as the CaMV(19S)-NPTII-NOS gene, was inserted into plasmid pMON120 (described in the parent application, Ser. No. 458,414; ATCC accession number 39263) to create a plasmid designated as pMON156. Plasmid pMON156 was inserted into an *Agrobacterium tumefaciens* cell, where it formed a co-integrate Ti plasmid by means of a single crossover event with a Ti plasmid in the *A. tumefaciens* cell, using a method described in the parent application. The chimeric gene in the co-integrate plasmid was within a modified T-DNA region in the Ti plasmid, surrounded by left and right T-DNA borders.

*A. tumefaciens* cells containing the co-integrate Ti plasmids with the CaMV(19S)-NPTII-NOS genes were used to infect plant cells, using a method described in the parent application. Some of the plant cells were genetically transformed, causing them to become resistant to an antibiotic (kanamycin) at concentrations which are toxic to untransformed plant cells.

A similar chimeric gene was created and assembled in a plasmid designated as pMON155. This chimeric gene resembled the gene in pMON156, with two exceptions:

1. an oligonucleotide linker having stop codons in all three reading frames was inserted between the CaMV(19S) partial structural sequence and the NPTII structural sequence; and,
2. the spurious ATG sequence on the 5' side of the NPTII structural sequence was deleted.

The construction of this chimeric gene is described in Example 2. This gene was inserted into *A. tumefaciens* cells and subsequently into plant cells. Its level of expression was apparently higher than the expression of the similar gene in pMON156, as assayed by growth on higher concentrations of kanamycin.

CREATION OF PLASMIDS pMON183 and 184; CaMV(35S)

In an alternate preferred embodiment of this invention, a chimeric gene was created comprising
  (1) a promoter region which causes transcription of the 35S mRNA of cauliflower mosaic virus, CaMV(35S);
  (2) a structural sequence which codes for NPTII; and
  (3) a nopaline synthase (NOS) 3' non-translated region.

The assembly of this chimeric gene is described in Example 3. This gene was inserted into plant cells and it caused them to become resistant to kanamycin.

Petunia plants cannot normally be infected by CaMV. Those skilled in the art may determine through routine experimentation whether any particular plant viral promoter (such as the CaMV promoter) will function at satisfactory levels in any particular type of plant cell, including plant cells that are outside of the normal host range of the virus from which the promoter was derived.

It is possible to regenerate genetically transformed plant cells into differentiated plants. One method for such regeneration was described in U.S. patent application entitled "Genetically Transformed Plants", Ser. No. 458,402, now abandoned. That application was filed simultaneously with, and incorporated by reference into, the parent application of this invention. The methods of application Ser. No. 458,402, now abandoned, may be used to create differentiated plants (and their progeny) which contain and express chimeric genes having plant virus promoters.

It is possible to extract polypeptides generated in plant cells by chimeric genes of this invention from the plant cells, and to purify such extracted polypeptides to a useful degree of purity, using methods and substances known to those skilled in the art.

Those skilled in the art will recognize, or may ascertain using no more than routine experimentation, numerous equivalents to the specific embodiments described herein. Such equivalents are within the scope of this invention, and are covered by the claims below.

EXAMPLES

Example 1: Creation and Use of pMON156

Plasmids which contained CaMV DNA were a gift to Monsanto Company from Dr. R. J. Shepherd, University of California, Davis. To the best of Applicants' knowledge and belief, these plasmids (designated as pOS1) were obtained by inserting the entire genome of a CaMV strain designated as CM4-184 (Howarth et al, 1981) into the Sal I restriction site of a pBR322 plasmid (Bolivar et al, 1978). $E.$ $coli$ cells transformed with pOS1 were resistant to ampicillin ($Amp^R$) and sensitive to tetracycline ($Tet^S$).

Figure 2:
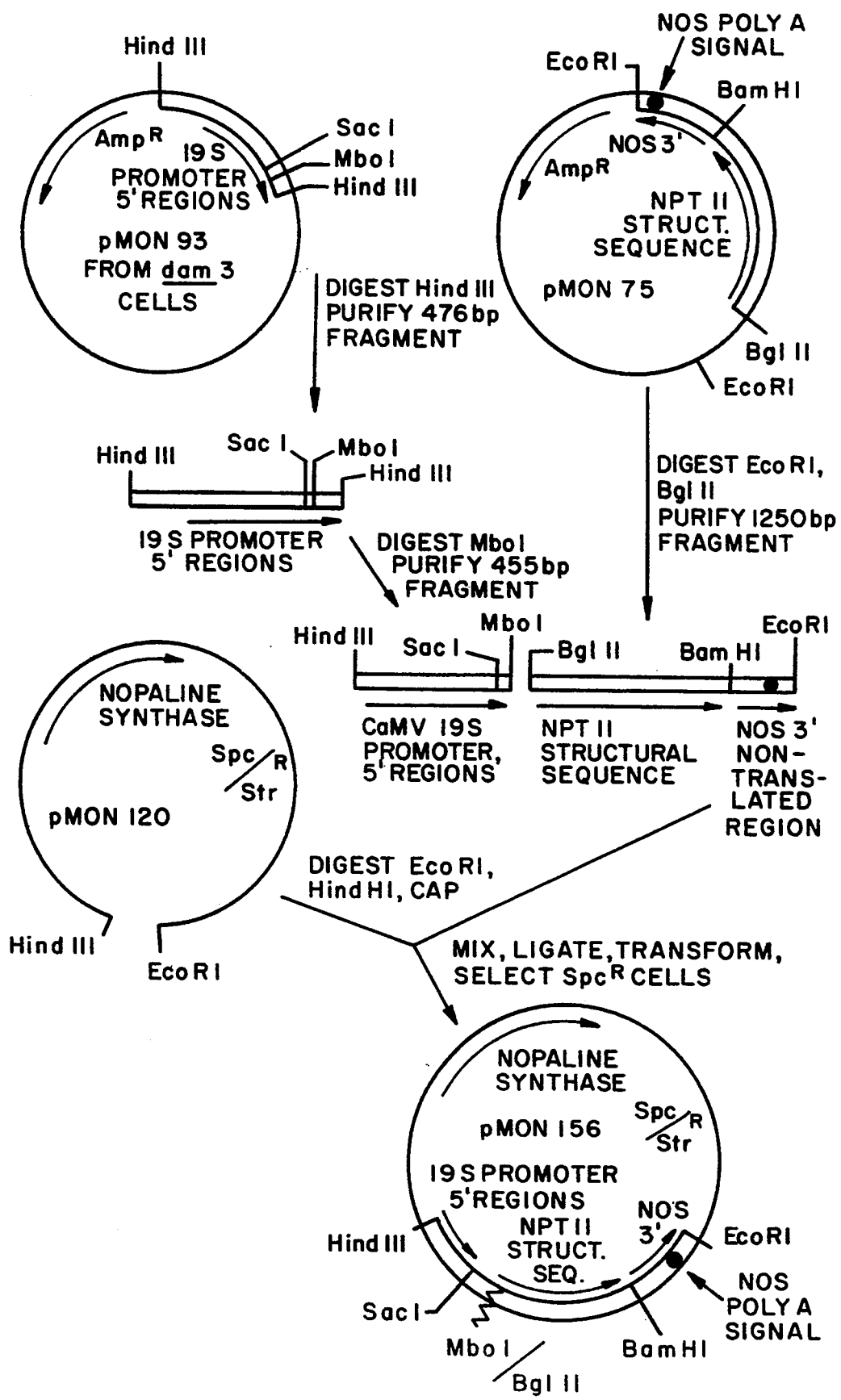
FIG. 2 represents the creation and structure of plasmid pMON156.
Figure 9:
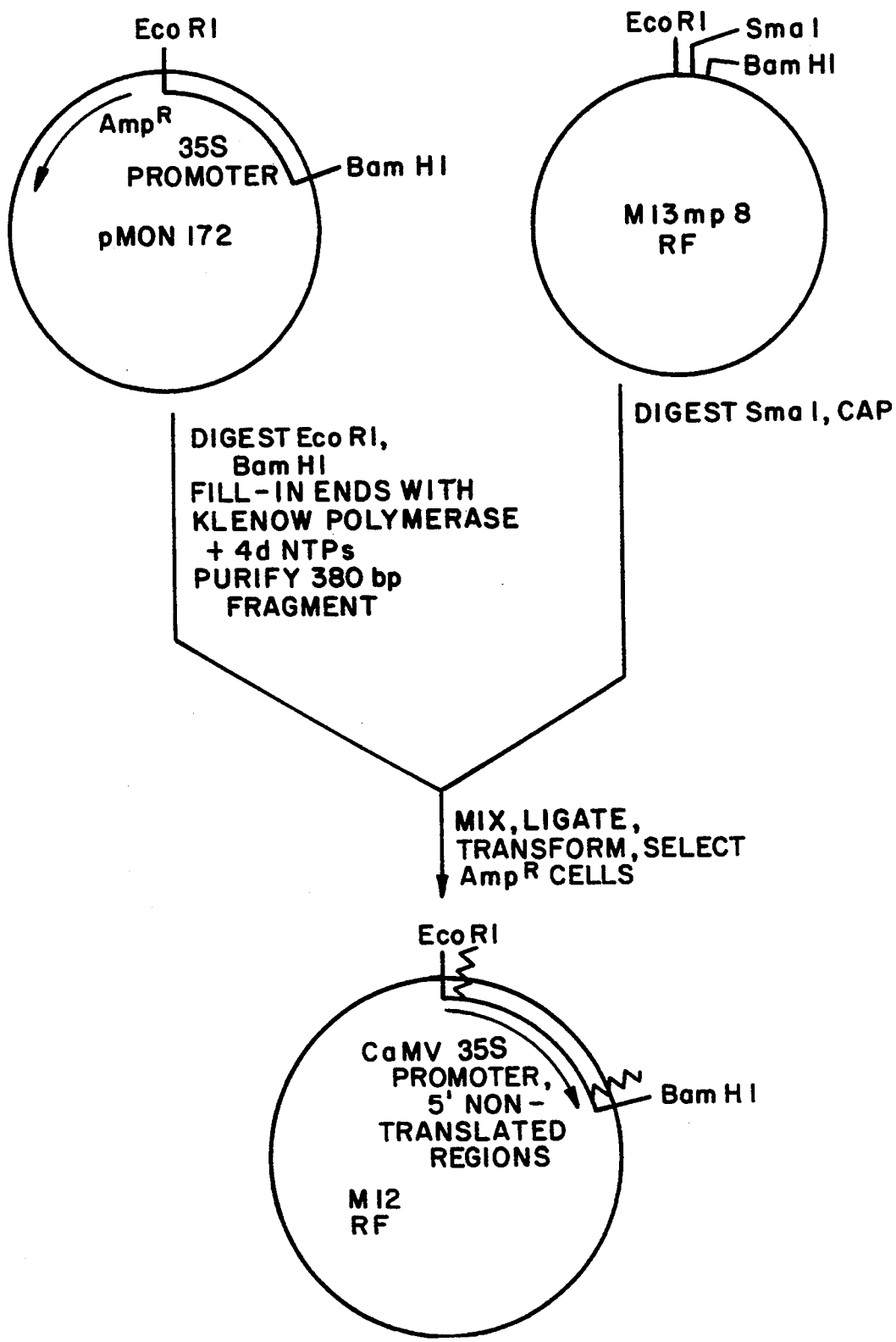
FIG. 9 represents the creation and structure of phage M12.
Figure 10:
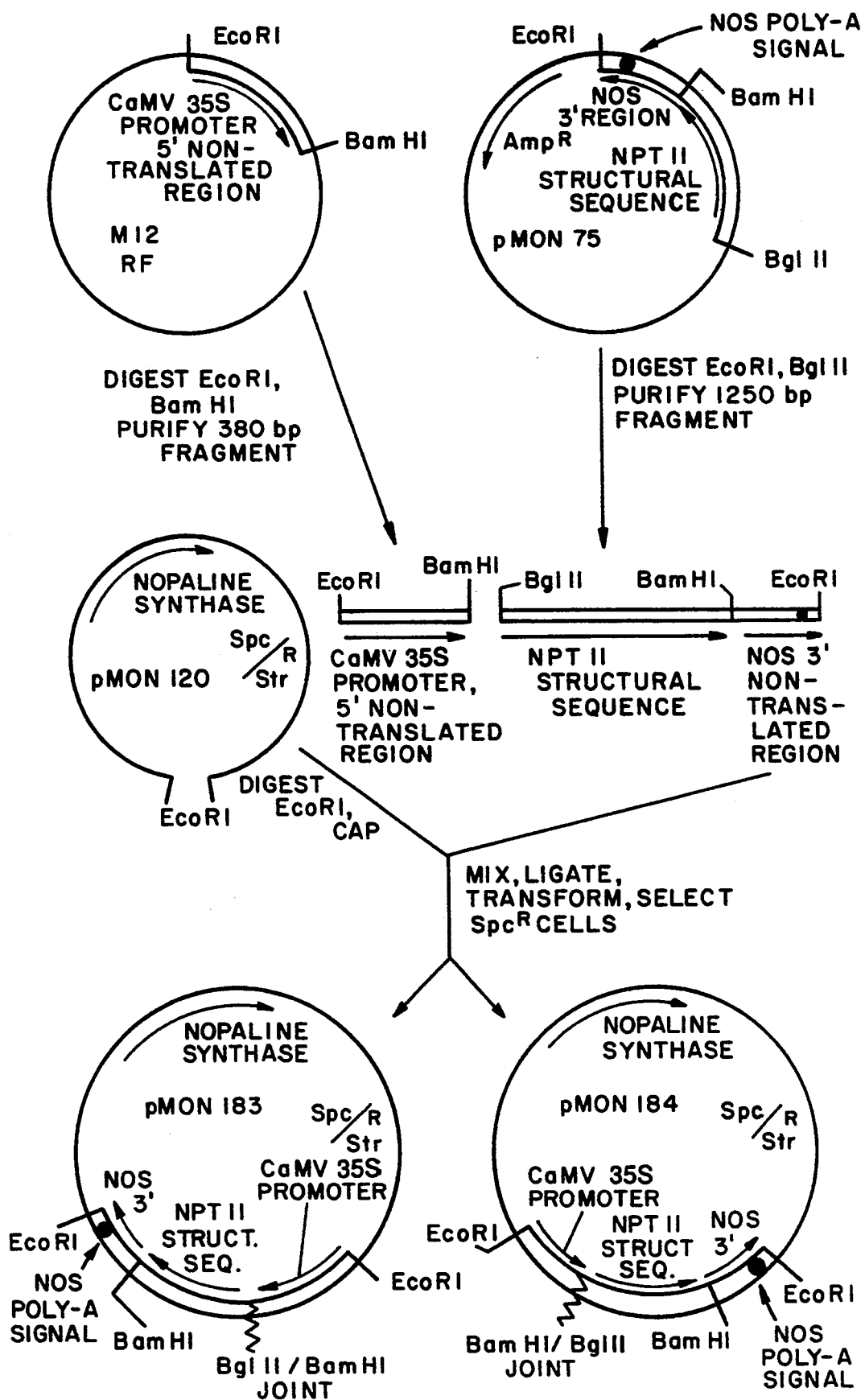
FIG. 10 represents the creation and structure of plasmids pMON183 and pMON184.

Various strains of CaMV suitable for isolation of CaMV DNA which can be used in this invention are publicly available; see, e.g., ATCC Catalogue of Strains II, p. 387 (3rd edition, 1981).

pOS1 DNA was cleaved with HindIII. Three small fragments were purified after electrophoresis on an 0.8% agarose gel using NA-45 membrane (Schleicher and Schuell, Keene NH). The smallest fragment, about 500 bp in size, contains the 19S promoter. This fragment was further purified on a 6% acrylamide gel. After various manipulations which did not change the sequence of this fragment (shown in FIG. 1), it was digested with MboI to created 455 bp HindIII-MboI fragment. This fragment was mixed with a 1250 bp fragment obtained by digesting pMON75 (described and shown in FIG. 9 of the parent application Ser. No. 458,414, now abandoned,) with BglII and EcoRI. This fragment contains the NPTII structural sequence and the NOS 3' non-translated region. The two fragments were ligated by their compatible MboI and BglII overhangs to create a fragment containing the CaMV(19S)-NPTII-NOS chimeric gene. This fragment was inserted into pMON120 (described and shown in FIG. 10 of the parent application, Ser. No. 458,414, now abandoned; ATCC accession number 39263) which had been cleaved with HindIII and EcoRI. The resulting plasmid was designated as pMON156, as shown in FIG. 2.

Plasmid pMON156 was inserted into $E.$ $coli$ cells and subsequently into $A.$ $tumefaciens$ cells where it formed a co-integrate Ti plasmid having the CaMV(19S)-NPTII-NOS chimeric gene surrounded by T-DNA borders. $A.$ $tumefaciens$ cells containing the co-integrate plasmids were co-cultivated with petunia cells. The foregoing methods are described in detail in a separate application, entitled "Plasmids for Transforming Plant Cells" Ser. No. 458,411, now abandoned, which was filed simultaneously with and incorporated by reference into parent application, Ser. No. 458,414, now abandoned.

The co-cultivated petunia cells were cultured on media containing kanamycin, an antibiotic which is toxic to petunia cells. Kanamycin is inactivated by the enzyme NPTII, which does not normally exist in plant cells. Some of the co-cultivated petunia cells survived and produced colonies on media containing up to 50 ug/ml kanamycin. This indicated that the CaMV(19S)-NPTII-NOS genes were expressed in petunia cells. These results were confirmed by Southern blot analysis of transformed plant cell DNA.

Example 2: Creation of pMON155

Plasmid pMON72 was obtained by inserting a 1.8 kb HindIII-BamHI fragment from bacterial transposon Tn5 (which contains an NPTII structural sequence) into a PstI⁻ pBR327 plasmid digested with HindIII and BamHI. This plasmid was digested with BglII and PstI to remove the NPTII structural sequence.

Plasmid pMON1001 (described and shown in FIG. 6 of the parent application) from dam⁻ cells was digested with BglII and PstI to obtain a 218 bp fragment with a partial NPTII structural sequence. This fragment was digested with MboI to obtain a 194 bp fragment.

Figure 3:
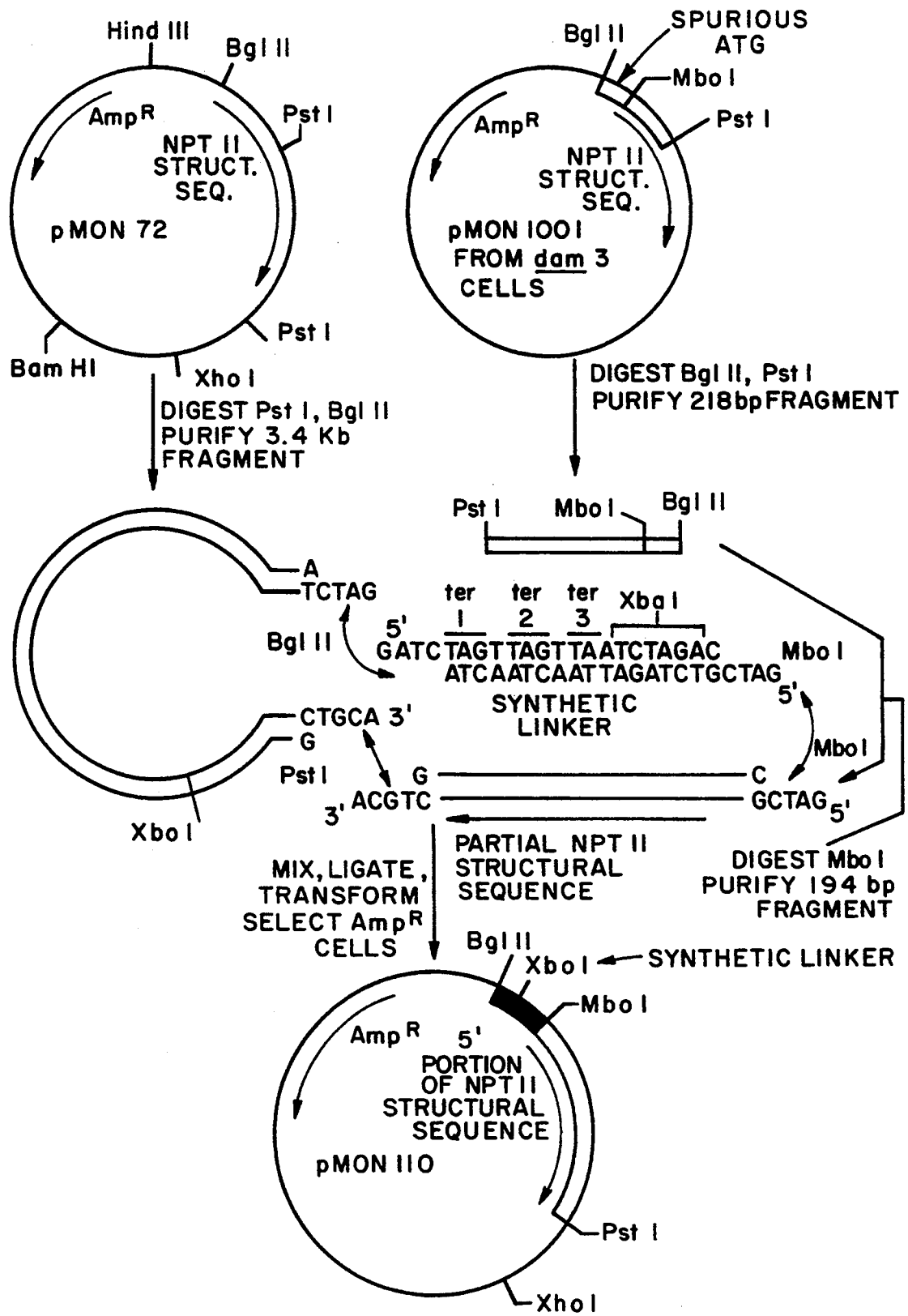
FIG. 3 represents the creation and structure of plasmid pMON110.

A triple ligation was performed using (a) the large PstI-BglII fragment of pMON72; (b) PstI-MboI fragment from pMON1001; and (c) a synthetic linker with BglII and MboI ends having stop codons in all three reading frames. After transformation of $E.$ $coli$ cells and selection for ampicillin resistant colonies, plasmid DNA from Amp $^R$ colonies was analyzed. A colony containing a plasmid with the desired structure was identified. This plasmid was designated pMON110, as shown on FIG. 3.

Figure 4:
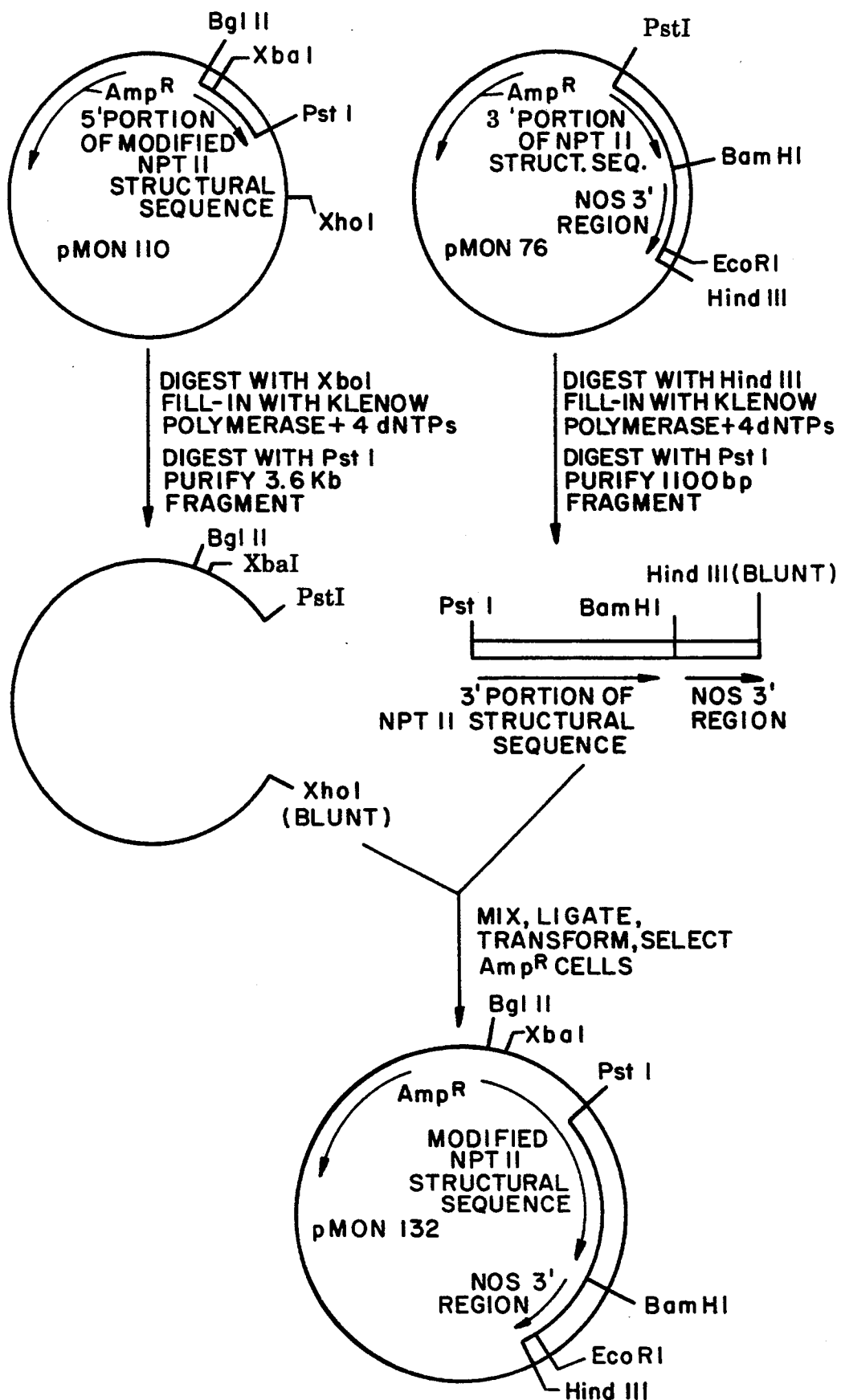
FIG. 4 represents the creation and structure of plasmid pMON132.

In order to add the 3' end of the NPTII structural sequence to the 5' portion in pMON110, pMON110 was treated with XhoI. The resulting overhanging end was filled in to create a blunt end by treatment with Klenow polymerase and the four deoxy-nucleotide triphosphates (dNTP's), A, T, C, and G. The Klenow polymerase was inactivated by heat, the fragment was digested with PstI, and a 3.6 kb fragment was purified. Plasmid pMON76 (described and shown in FIG. 9 of the parent application) was digested with HindIII, filled in to create a blunt end with Klenow polymerase and the four dNTP's, and digested with PstI. An 1100 bp fragment was purified, which contained part of the NPTII structural sequence, and a nopaline synthase (NOS) 3' non-translated region. This fragment was ligated with the 3.6 kb fragment from pMON110. The mixture was used to transform $E.$ $coli$ cells; Amp R cells were selected, and a colony having a plasmid with the desired structure was identified. This plasmid was designated pMON132, as shown on FIG. 4. Plasmid pMON93 (shown on FIG. 1) was digested with HindIII, and a 476 bp fragment was isolated. This fragment was digested with MboI, and a 455 bp HindIII-MboI fragment was purified which contained the CaMV (19S) promoter region, and 5' non-translated region.

Plasmid pMON132 was digested with EcoRI and BglII to obtain a 1250 bp fragment with (1) the synthetic linker equipped with stop codons in all three reading frames; (2) the NPTII structural sequence; and (3) the NOS 3' non-translated region. These two fragments were joined together through the compatible MboI nd BglII ends to create a CaMV (19S)-NPTII-NOS chimeric gene.

Figure 5:
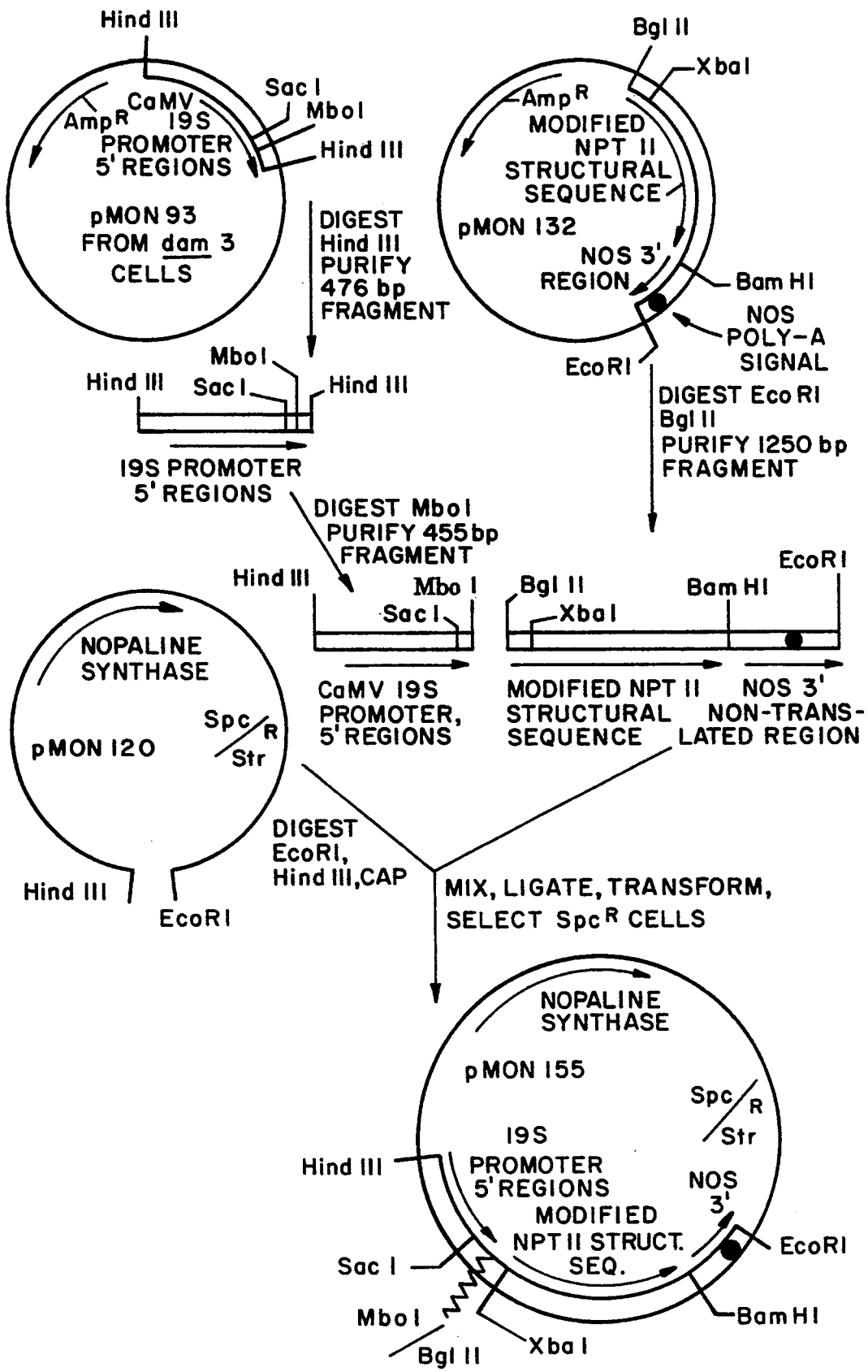
FIG. 5 represents the creation and structure of plasmid pMON155.

This gene was inserted into pMON120, which was digested with HindIII and EcoRI, to create plasmid pMON155, as shown in FIG. 5.

Plasmid pMON155 was inserted into *A. tumefaciens* GV3111 cells containing a Ti plasmid, pTiB6S3. The pMON155 plasmid formed a cointegrate plasmid with the Ti plasmid by means of a single crossover event. Cells which contain this co-integrate plasmid have been deposited with the American Type Culture Center, and have been assigned ATCC accession number 39336. A fragment which contains the chimeric gene of this invention can be obtained by digesting the co-integrate plasmid with HindIII and EcoRI, and purifying the 1.7 kb fragment. These cells have been used to transform petunia cells, allowing the petunia cells to grow on media containing at least 100 ug/ml kanamycin.

Example 3: Creation of pMON183 and 184

Plasmid pOS1 (described in Example 1) was digested with BglII, and a 1200 bp fragment was purified. This fragment contained the 35S promoter region and part of the 5' non-translated region. It was inserted into plasmid pSHL72 which had been digested with BamHI and BglII (pSHL72 is functionally equivalent to pAGO60, described in Colbere-Garapin et al, 1981). The resulting plasmid was designated as pMON50, as shown on FIG. 6.

Figure 6:
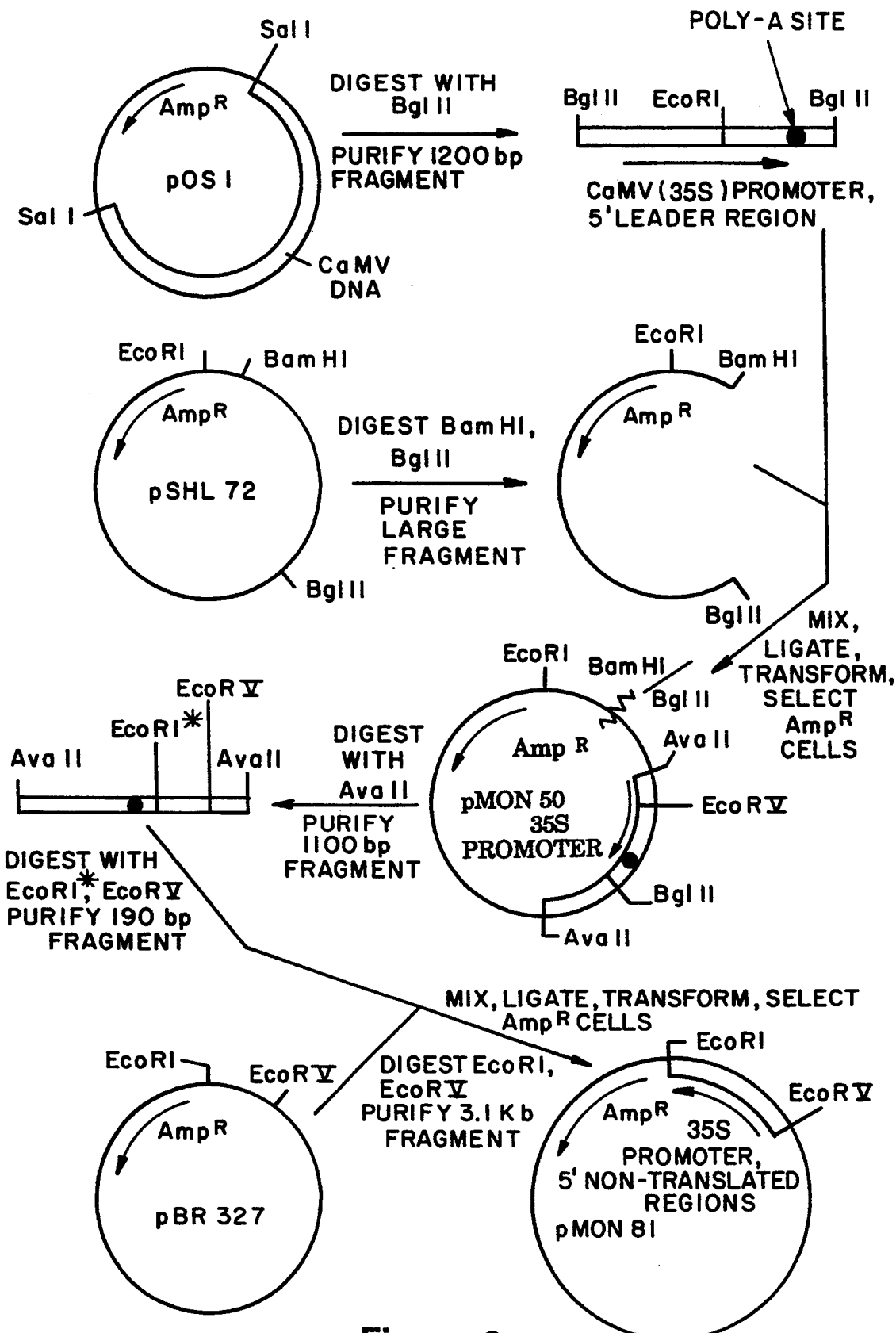
FIG. 6 represents the creation and structure of plasmid pMON81.

The cloned BglII fragment contains a region of DNA that acts as a polyadenylation site for the 35S RNA transcript. This polyadenylation region was removed as follows: pMON50 was digested with AvaII and an 1100 bp fragment was purified. This fragment was digested with EcoRI* and EcoRV. The resulting 190 bp EcoRV-EcoRI* fragment was purified and inserted into plasmid pBR327, which had been digested with EcoRI* and EcoRV. The resulting plasmid, pMON81, contains the CaMV 35S promoter on a 190 bp EcoRV-EcoRI* fragment, as shown in FIG. 6.

Figure 7:
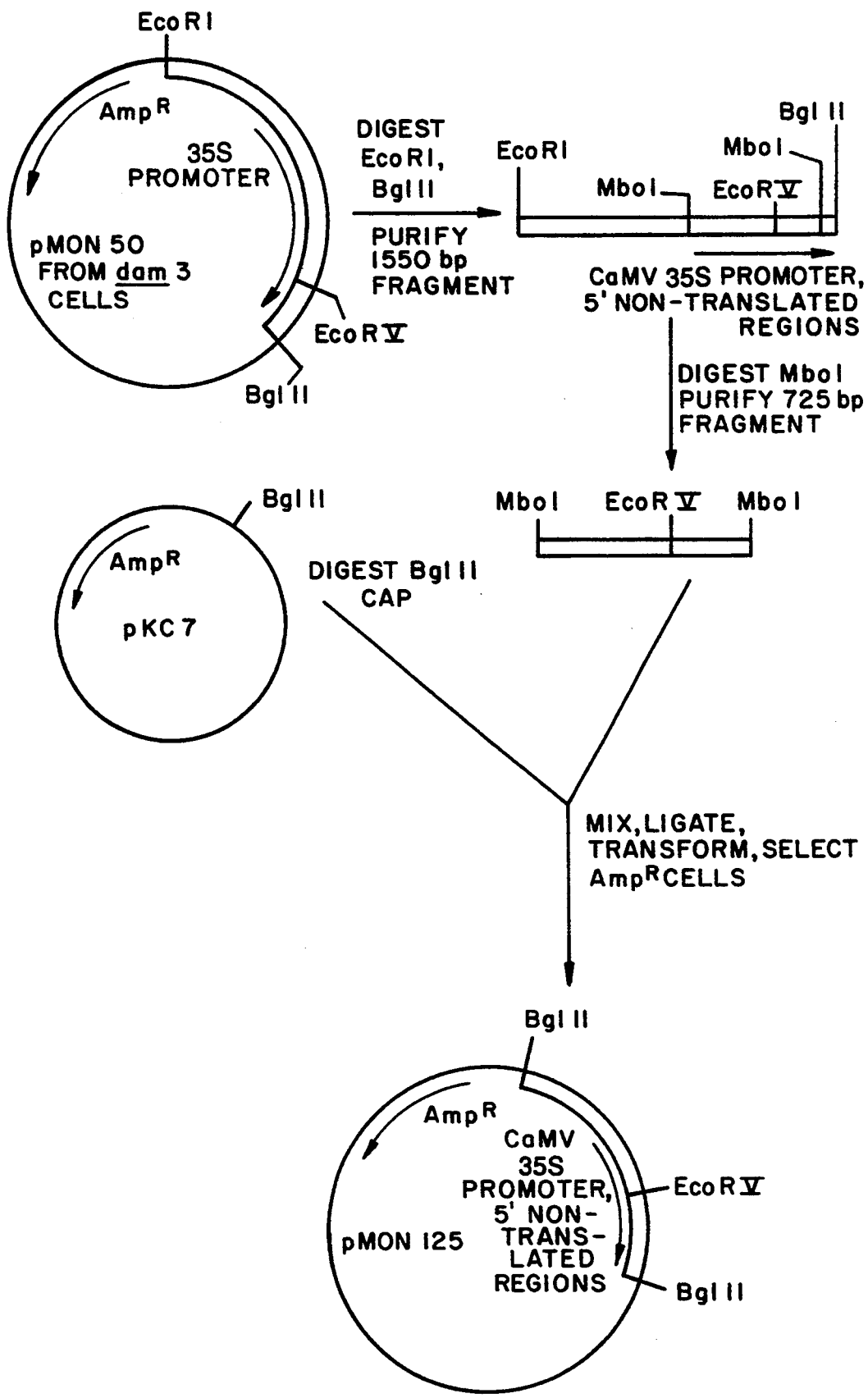
FIG. 7 represents the creation and structure of plasmid pMON125.

To make certain the entire promoter region of CaMV(35S) was present in pMON81, a region adjacent to the 5' (EcoRV) end of the fragment was inserted into pMON81 in the following way. Plasmid pMON50 prepared from dam⁻ cells was digested with EcoRI and BglII and the resultant 1550 bp fragment was purified and digested with MboI. The resulting 725 bp MboI fragment was purified and inserted into the unique BglII site of plasmid pKC7 (Rao and Rogers, 1979) to give plasmid pMON125, as shown in FIG. 7. The sequence of bases adjacent to the two MboI ends regenerates BglII sites and allows the 725 bp fragment to be excised with BglII.

Figure 8:
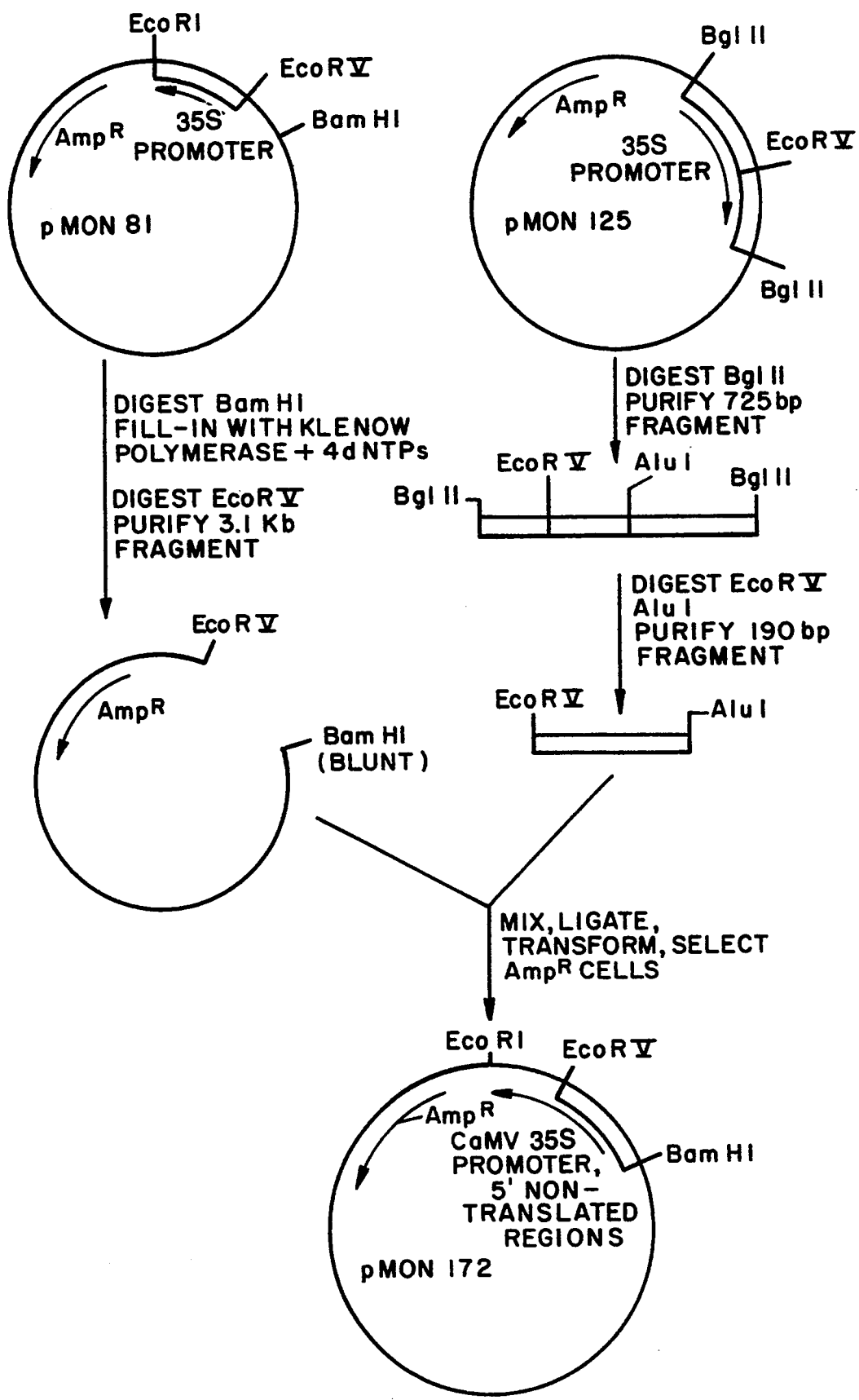
FIG. 8 represents the creation and structure of plasmid pMON172.

To generate a fragment carrying the 35S promoter, the 725 bp BglII fragment was purified from pMON125 and was subsequently digested with EcoRV and AluI to yield a 190 bp fragment. Plasmid pMON81 was digested with BamHI, treated with Klenow polymerase and digested with EcoRV. The 3.1 kb EcoRV-BamHI(-blunt) fragment was purified, mixed with the 190 bp EcoRV-AluI fragment and treated with DNA ligase. Following transformation and selection of ampicillin-resistant cells, plasmid pMON172 was obtained which carries the CaMV(35S) promoter sequence on a 380 bp BamHI-EcoRI fragment, as shown on FIG. 8. This fragment does not carry the polyadenylation region for the 35S RNA. Ligation of the AluI end to the filled-in BamHI site regenerates the BamHI site.

To rearrange the restriction endonuclease sites adjacent to the CaMV(35S) promoter, the 380 bp BamHI-EcoRI fragment was purified from pMON172, treated with Klenow polymerase, and inserted into the unique smaI site of phage M13 mp8. One recombinant phage, M12, carried the 380 bp fragment in the orientation shown on FIG. 9. The replicative form DNA from this phage carries the 35S promoter fragment on an EcoRI(-5')-BamHI(3') fragment, illustrated below.

```
      EcoRI
   1  |          .          .          .          .          .          .         70
   GAATTCCCGATCc TATCTGTCACTTCATCAAAAGGACAGTAGAAAAGGAAGGTGGCACTACAAATGCCAT
  71             .          .          .          .          .          .        140
   CATTGCGATAAAGGAAAGGCTATCGTTCAAGATGCCTCTGCCGACAGTGGTCCCAAAGATGGACCCCCAC
 141             .          .          .          .          .          .        210
   CCACGAGGAGCATCGTGGAAAAAGAAGACGTTCCAACCACGTCTTCAAAGCAAGTGGATTGATGTGATAT
                                                                        TATA
 211             .          .          .          .          .          |        280
   CTCCACTGACGTAAGGGATGACGCACAATCCACTATACCTTCGCAAGACCCTTCCTCTATATAAGGAAGT
                 5'mRNA
 281             |          .          .          .          .          .        350
   TCATTTCATTTGGAGAGGACACGCTGAAATCACCAGTCTCTCTCTACAAATCTATCTCTCTATTTCT
           Extra Translational Initiator                        BamHI
 351     |.         .          .          .          .          |
   CCATAATAATGTGTGAGTAGTTCCCAGATAAGGGAATTGGGGATCC
```

Plasmids carrying a chimeric gene CaMV(35S) promoter region-NPTII structural sequence-NOS 3' non-translated region) were assembled as follows. The 380 bp EcoRI-BamHI CaMV(35S) promoter fragment was purified from phage M12 RF DNA and mixed with the 1250 bp BglII-EcoRI NPTII-NOS fragment from pMON75. Joining of these two fragments through their compatible BamHI and BglII ends results in a 1.6 kb CaMV(35S)-NPTII-NOS chimeric gene. This gene was inserted into pMON120 at the EcoRI site in both orientations. The resultant plasmids, pMON183 and 184, appear in FIG. 10. These plasmids differ only in the direction of the chimeric gene orientation.

These plasmids were used to transform petunia cells, as described in Example 1. The transformed cells are capable of growth on media containing 100 ug/ml kanamycin.

COMPARISON OF CaMV(35S) AND NOS PROMOTERS

Chimeric genes carrying the nopaline synthase (NOS) promoter or the cauliflower mosaic virus full-length transcript promoter (CaMV(35S)) were constructed. In both cases, the promoters, which contain their respective 5' non-translated regions were joined to al., 1982). The CaMV(35S) promoter sequence described above is listed below.

pMON273 CaMV 35S Promoter and 5' Leader

```
EcoRI
1  |                                                                    70
   GAATTCCCGATCc TATCTGTCACTTCATCAAAAGGACAGTAGAAAAGGAAGGTGGCACTACAAATGCCAT
71                                                                     140
   CATTGCGATAAAGGAAAGGCTATCGTTCAAGATGCCTCTGCCGACAGTGGTCCCAAAGATGGACCCCCAC
141                                                                    210
   CCACGAGGAGCATCGTGGAAAAAGAAGACGTTCCAACCACGTCTTCAAAGCAAGTGGATTGATGTGATAT
                                                                TATA
211                                                             |      280
   CTCCACTGACGTAAGGGATGACGCACAATCCACTATACCTTCGCAAGACCCTTCCTCTATATAAGGAAGT
          5'mRNA                                    BglII
281        |                                          |    334
   TCATTTCATTTGGAGAGGACACGCTGAAATCACCAGTCTCTCTCTACAAGATCT
``` a NPTII coding sequence in which the bacterial 5' leader had been modified so that a spurious ATG translational initiation signal (Southern and Berg, 1982) has been removed.

Plasmid pMON200 is a derivative of previously described intermediate vector pMON120 (ATCC accession number 39263). pMON200 contains a modified chimeric nopaline synthase-neomycin phosphotransferasenopaline synthase gene (NOS/NPTII/NOS) which confers kanamycin (Km$^R$) resistance to the transformed plant. The modified chimeric Km$^R$ gene lacks an upstream ATG codon present in the bacterial leader sequence and a synthetic multilinker with unique HindIII, XhoI, BglII, XbaI, ClaI and EcoRI restriction sites.

Plasmid pMON273 is a derivative of pMON200 in which the nopaline synthase promoter of the chimeric NOS-NPTII-NOS gene has been replaced with the CaMV(35S) promoter.

The CaMV(35S) promoter fragment was isolated from plasmid pOS-1, a derivative of pBR322 carrying the entire genome of CM4-184 as a SalI insert (Howarth et al., 1981). The CM4-184 strain is a naturally occurring deletion mutant of strain CM1841. The nucleotide sequence of the CM1841 (Gardner et al., 1981) and Cabb-S (Franck et al., 1980) strains of CaMV have been published as well as some partial sequence for a different CM4-184 clone (Dudley et al., 1982). The nucleotide sequences of the 35S promoter regions of these three isolates are essentially identical. In the following the nucleotide numbers reflects the sequence of Gardner et al. (1981). The 35S promoter was isolated as an AluI (n 7143)-EcoRI* (n 7517) fragment which was inserted first into pBR322 cleaved with BamHI, treated with the Klenow fragment of DNA polymerase I and then cleaved with EcoRI. The promoter fragment was then excised from pBR322 with BamHI and EcoRI, treated with Klenow polymerase and inserted into the SmaI site of M13 mp8 so that the EcoRI site of the mp8 multilinker was at the 5' end of the promoter fragment. Site directed mutagenesis (Zoller and Smith, 1982) was then used to introduce a G at nucleotide 7464 to create a BglII site. The 35S promoter fragment was then excised from the M13 as a 330 bp EcoRI-BglII site. The 35S promoter fragment was then excised from the M13 as a 330 bp EcoRI-BglII fragment which contains the 35S promoter, 30 nucleotides of the 5' non-translated leader but does not contain any of the CaMV translational initiators nor the 35S transcript polyadenylation signal that is located 180 nucleotides downstream from the start of transcription (Covey et al., 1981; Guilley et The 35S promoter fragment was joined to a 1.3 kb BglII-EcoRI fragment containing the Tn5 neomycin phosphotransferase II coding sequence modified so that the translational initiator signal in the bacterial leader sequence had been removed and the NOS 3' non-translated region and inserted into pMON120 to give pMON273.

These plasmids were transferred in *E. coli* strain JM101 and then mated into *Agrobacterium tumefaciens* strain GV3111 carrying the disarmed pTiB6S3-SE plasmid as described by Fraley et al. (1983).

Plant Transformation

Cocultivation of Petunia protoplasts with *A. tumefaciens*, selection of kanamycin resistant transformed callus and regeneration of transgenic plants was carried out as described in Fraley et al. (1984).

Preparation of DNAs

Plant DNA was extracted by grinding the frozen tissue in extraction buffer (50 mM TRIS-HCl pH 8.0, 50 mM EDTA, 50 mM NaCl, 400 ul/ml EtBr, 2% sarcosyl). Following low speed centrifugation, cesium chloride was added to the supernatant (0.85 gm/ml). The CsCl gradients were centrifuged at 150,000×g for 48 hours. The ethidium bromide was extracted with isopropanol, the DNA was dialyzed, and ethanol precipitated.

Southern Hybridization Analysis 10 ug of each plant DNA was digested, with BamHI for pMON200 plant DNAs and EcoRI for pMON273 plant DNAs. The fragments were separated by electrophoresis on a 0.8% agarose gel and transferred to nitrocellulose (Southern, 1975). The blots were hybridized (50% formamide, 3xSSC, 5X denhardt's, 0.1% SDS and 20 ug/ml tRNA) with nick-translated pMON273 plasmid DNA for 48–60 hours at 42° C.

Preparation of RNA from Plant Tissue

Plant leaves were frozen in liquid nitrogen and ground to a fine powder with a mortar and pestle. The frozen tissue was added to a 1:1 mixture of grinding buffer and PCE (1% Tri-iso-propylnaphtalenesulfonic acid, 6% p-Aminosalicylic acid, 100 mM NaCl, 1% SDS and 50 mM 2-mercaptoethanol; PCI [phenol: chloroform: isoamyl alcohol (24:24:1)] and homogenized immediately with a polytron. The crude homogenate was mixed for 10 min and the phases separated by centrifugation. The aqueous phase then was re-extracted with an equal volume of PCI. The aqueous phase was ethanol precipitated with one tenth volume of 3M NaAcetate and 2.5 volumes of ethanol. The nucleic acid pellet was resuspended in water. An equal volume of 4M lithium chloride LiCl was added and the mix was placed on ice for 1 hour or overnight. Following centrifugation, the pellet was resuspended in water the LiCl precipitation repeated 3 times. The final LiCl pellet was resuspended in water and ethanol precipitated.

Poly (A) containing RNA was isolated by passing total RNA over an Oligo d(T) cellulose Type III (Collaborative Research) column. Quantitation of the poly (A) containing RNA involved annealing an aliquot of the RNA to radio-labeled poly U [(uridylate 5,6-3H)-polyuridylic acid] (New England Nuclear), followed by RNase A treatment (10 ug per ml for 30 minutes at 37° C.). The reaction mix was spotted on DE-81 filter paper, washed 4× with 0.5M NaPhosphate (pH 7.5) and counted. Globin poly (A) containing RNA (BRL) was used as a standard.

Northern Hybridization Analysis 5 ug of poly (A) RNA from each plant source was treated with glyoxal and dimethysulfoxide (Maniatis, 1982). The RNAs were electrophoresed in 1.5% agarose gels (0.01M $NaH_2HPO_4$, pH 6.5) for 7 hours at 60 volts. The glyoxylated RNAs were electro-blotted (25 mM $NaH_2PO_4NaHPO_4$, pH 6.5) for 16 hours at 125 amps from the gel to GeneScreen® (New England Nuclear). The filters were hybridized as per manufacturer's instructions (50% formamide, 0.02% polyvinylpyrrolidone, 0.02% bovine serum albumin, 0.02% ficoll, 5XSSC, 1.0% SDS, 100 u/ml tRNA and probe) for 48–60 hours at 42° C. with constant shaking. The nick-translated DNAs used as probes were the 1.3 kb BglII/EcoRI NPTII fragment purified from the pMON273 plasmid for detecting the NPTII transcript, and the petunia small subunit gene as an internal standard for comparing the amount of RNA per lane. The membranes were washed 2×100 ml of 2XSSC at room temperature for 5 minutes, 2×100 ml of 2XSSC/1.0% SDS at 65° C. for 30 minutes. The membranes were exposed to XAR-5 film with a DuPont intensifying screen at −80° C.

Neomycin Phosphotransferase Assay

The gel overlay assay was used to determine the steady state level of NPTII enzyme activity in each plant. Several parameters were investigated for optimizing the sensitivity of the assay in plant tissue. Early observations showed that the level of NPTII activity varied between leaves from different positions on the same plant. This variability was minimized when the plant extract was made from pooled tissue. A paper hole punch was used to collect 15 disks from both young and old leaves. Grinding the plant tissue in the presence of micro-beads (Ferro Corp) rather than glass beads increased the plant protein yield 4-fold.

To optimize detection of low levels of NPTII activity a saturation curve was prepared with 10–85 ug/lane of plant protein. For the pMON200 (NOS) plants, NPTII activity was not detectable at less than 50 ug/lane of total protein (2 hour exposure) while activity was detectable at 20 ug/lane for the pMON273 plants. There was a non-linear increase in NPTII activity for pMON200 NOS plants between 40 and 50 ug of protein per lane. This suggested that the total amount of protein may affect the stability of the NPTII enzyme. Supplementing plant cell extracts with 30–45 ug per lane of bovine serum albumin (BSA), resulted in a linear response; NPTII activity increased proportionately as plant protein levels increased. The addition of BSA appears to stabilize the enzyme, resulting in a 20-fold increase in the sensitivity of the assay. Experiments indicate that 25 ug/lane of pMON273 plant protein and 70 ug/lane of pMON200 plant protein was within the linear range of the assay in the presence of BSA. Elimination of SDS from the extraction buffer resulted in a 2-fold increase in assay sensitivity. Leaf disks were pooled from each plant for the assay. The tissue was homogenized with a glass rod in a microfuge tube with 150–200 ul of extraction buffer (20% glycerol, 10% β-mercaptoethanol, 125 mM Tris-HCl pH 6.8, 100 ug/ml bromophenol blue and 0.2% SDS). Following centrifugation in a microfuge for 20 minutes, total protein was determined using the Bradford assay. 25 ug of pMON273/3111SE plant protein or 70 ug of pMON200/3111SE plant protein, supplemented with BSA, was loaded on a native polyacrylamide gel as previously described. The polyacrylamide gel was equilibrated for 30 minutes in water and then 30 minutes in reaction buffer (67 mM TRIS-maleate pH 7.1, 43 mM $MgCl_2$, 400 mM $NH_4Cl$), transferred onto a glass plate, and overlaid with a 1.5% agarose gel. The overlay gel contained the neomycin phosphotransferase substrates: 450 uCi [$\gamma$-$^{32}$] ATP and 27 ug/ml neomycin sulfate (Sigma). After 1 hour at room temperature a sheet of Whatman P81 paper, two sheets of Whatman 3MM paper, a stack of paper towels and a weight were put on top of the agarose gel. The phosphorylated neomycin is positively charged and binds to the P81 phosphocellulose ion exchange paper. After blotting overnight, the P81 paper was washed 3× in 80° C. water, followed by 7 room temperature washes. The paper was air dried and exposed to XAR-5 film. Activity was quantitated by counting the $^{32}P$-radioactivity in the NPTII spot. The NPTII transcript levels and enzyme activities in two sets of transgenic petunia plants were compared. In one set of plants (pMON273) the NPTII coding sequence is preceded by the CaMV(35S) promoter and leader sequences, in the other set of plants (PMON200) the NPTII coding region is preceded by the nopaline synthase promoter and leader sequences. The data indicates the pMON273 plants contain about a 30 fold greater level of NPTII transcript than the pMON200 plants, see Table I below.

TABLE I

QUANTITATION OF NPTII TRANSCRIPT LEVELS AND NPTII ACTIVITY IN pMON273 AND pMON200 PLANTS

| Plant Number | Relative NPTII Transcript[a] | Relative NPTII Activity[b] |
|---|---|---|
| pMON 273 | | |
| 3272 | 682 | 113 |
| 3271 | 519 | 1148 |
| 3349 | 547 | 447 |
| 3350 | 383 | 650 |
| 3343 | 627 | 1539 |
| Average | 551 | 779 |
| pMON 200 | | |
| 2782 | 0 | 0.22 |
| 2505 | 0 | 5.8 |
| 2822 | 0 | 0 |
| 2813 | 34 | 19 |
| 2818 | 0 | 1.0 |
| 3612 | 45 | 0.33 |
| 2823 | 97 | 23 |
| Average | 19 | 7 |
| | ~30-fold | ~110-fold |

TABLE I-continued

QUANTITATION OF NPTII TRANSCRIPT LEVELS AND NPTII ACTIVITY IN pMON273 AND pMON200 PLANTS

| Plant Number | Relative NPTII Transcript[a] | Relative NPTII Activity[b] |
|---|---|---|
| | difference | difference |

[a]Numbers derived from silver grain quantitation of autoradiogram. The RNA per lane was determined by filter hybridization to a petunia small subunit gene. The NPTII transcript values obtained with the NPTII probe were normalized for the amount of RNA in each lane.
[b]Numbers represent quantitation of NPT assay. Values were obtained by scintillation counting of 32-P-NPTII spots on the PE-81 paper used in the NPT assay as previously described. Values have been adjusted for the different amounts of protein loaded on the gels (25 ug) for pMON273 and 70 ug for pMON200 plants).

Consistent with this observation is the finding that the pMON273 leaf extracts have higher NPTII enzyme activity than the pMON200 leaf extracts. In several of the transgenic plants, there is a substantial variation in both RNA and enzyme levels which cannot be accounted for by the slight difference in gene copy number. Such "position effects" have been reported in transgenic mice and fruit flies and have not yet been adequately explained at the molecular level. Although, there is not a clear correlation between insert copy number and level of chimeric gene expression, the fact that 4 of the 7 pMON200 transgenic plants contain 2 copies of the NOS-NPTII-NOS gene would suggest that the differential expression of the CaMV(35S) promoter is actually slightly underestimated in these studies.

The constructs described in this comparative example have identical coding regions and 3' non-translated regions, indicating that the differences in the steady state transcript levels of these chimeric genes is a result of the 5' sequences.

COMPARISON OF CaMV19S AND CaMV(35S) PROMOTERS

Chimeric genes were prepared comprising either the CaMV19S or CaMV(35S) promoters. As in the above example, the promoters contained their respective 5' non-translated regions and were joined to a NPTII coding sequence in which the bacterial 5' leader had been modified to remove a spurious ATG translational initiation signal. The constructs tested were pMON203 and pMON204 containing the CaMV19S/NPTII/NOS gene and pMON273 containing the CaMV(35S)/NPTII/NOS gene.

Construction of pMON203

The CaMV 19S promoter fragment was isolated from plasmid pOS-1, a derivative of pBR322 carrying the entire genome of CM4-184 as a SalI insert (Howarth et al., 1981). The CM4-184 strain is a naturally occurring deletion mutant of strain CM1841. The references to nucleotide numbers in the following discussion are those for the sequence of CM1841 (Gardner et al., 1981). A 476 bp fragment extending from the HindIII site at bp 5372 to the HindIII site at bp 5848 was cloned into M13 mp8 for site directed mutagenesis (Zoller and Smith, 1982) to insert an XbaI (5'-TCTAGA) site immediately 5' of the first ATG translational initiation signal in the 19S transcript (Dudley et al., 1982). The resulting 400 bp HindIII-XbaI fragment was isolated and joined to the 1.3 kb XbaI-EcoRI fragment of pMON273 which carries the neomycin phosphotransferase II (NPTI') coding sequence modified so that the extra ATG translational initiation signal in the bacterial leader had been removed and the nopaline synthase 3' nontranslated region (NOS). The resulting 1.7 kb HindIII-EcoRI fragment was inserted into pMON120 between the EcoRI and HindIII sites to give pMON203. The complete sequence of the 19S promoter-NPTII leader is given below.

```
     HindIII
    1|                    .          .          .          .          .         70
    AAGCTTTAAAGCTGCAGAAAGGAATTACCACAGCAATGACAAAGAGACATTGGCGGTAATAAATACTATA
    71         .          .          .          .          .          .        140
    AAGAAATTCAGTATTTATCTAACTCCTGTTCATTTTCTGATTAGGACAGATAATACTCATTTCAAGAGTT
    141        .          .          .          .          .          .        210
    TTGTTAACCTTAATTACAAAGGAGATTCAAAACTTGGAAGAAACATCAGATGGCAAGCATGGCTTAGCCA
    211        .          .          .          .          .          .        280
    CTATTCGTTTGATGTTGAACATATTAAAGGAACCGACAACCACTTTGCGGACTTCCTTTCAAGAGAATTC
    281        .          .          .          .          .          .        350
    AATAAGGTTAATTCCTAATTGAAATCCGAAGATAAGATTCCCACACACTTGTGGCTGATATCAAAAAGGC
          TATA                                       5'   mRNA
    351     |             .          .            . | | |              402
    TACTACCTATATAAACACATCTCTGGAGACTGAGAAAATCAGACCTCCAAGC
      XbaI                 NPTII Initiator Signal
      |                       |
    TCTAGACGATCGTTTCGC      ATG
```

Construction of pMON204

The 400 bp HindIII-XbaI fragment containing the CaMV19S promoter was joined to a synthetic linker with the sequence:

```
     XbaI                BglII
      |                    |
    5'-TCTAGACTCCTTACAACAGATCT
``` to add a BglII site to the 3' end of the promoter fragment. The HindIII-BglII fragment was joined to the 1.3 kb BglII-EcoRI fragment of pMON128 that contains the natural, unmodified NPTII coding sequence joined to the NOS 3' nontranslated signals and inserted into the EcoRI and HindIII sites of pMON120. The resulting plasmid is pMON204. The CaMV 19S promoter signals in this plasmid are identical to those in pMON203. The only difference is the sequence of the 5' nontranslated leader sequence which in pMON204 contains the extra ATG signal found in the bacterial leader of NPTII and contains extra bases from the synthetic linker and bacterial leader sequence.

Petunia leaf discs were transformed and plants regenerated as described above. The gel overlay assay was used to determine NPTII levels in transformants.

Quantitation was done by scintillation counting of $^{32}$P-neomycin, the end product of neomycin phosphotransferase activity. The average NPTII enzyme level determined for CaMV(35S) (pMON273) plants was 3.6 times higher than that determined for CaMV(19S) (pMON203 & 204) plants.

QUANTITATION OF NPTII ACTIVITY LEVELS
IN pMON203, pMON204, AND pMON273 PLANTS

| Construct | Plant Number | Relative NPTII Activity[a] | Average | |
|---|---|---|---|---|
| pMON203 | 4283 | 499,064 | 398,134 | |
| pMON203 | 4248 | 297,204 | | |
| | | | | 356,203 |
| pMON204 | 4275 | 367,580 | 314,273 | |
| pMON204 | 4280 | 260,966 | | |
| pMON273 | 3350 | 1,000,674 | 1,302,731 | |
| pMON273 | 3271 | 1,604,788 | | |

$$\frac{35s}{19s} \quad \frac{1,302,721}{356,203} \approx 3.6$$

[a]Numbers represent quantitation of NPT assay. Values were obtained by scintillation counting of $^{32}$P-NPTII spots on the PE-81 paper used in the NPT assay as previously described.

REFERENCE

F. Bolivar, *Gene* 4: 121 (1978)
F. Colbere-Garapin et al, *J. Mol. Biol.* 150: 1 (1981)
S. N. Covey, G. P. Lomonosoff and R. Hull (1981) *Nucleic Acids Res.* 9, 6735–6747.
R. Dudley et al (1982) *Virology* 117: 19.
R. T. Fraley, et al. (1983) *Proc. Natl. Acad. Sci. USA* 80:4803–4807.
R. T. Fraley, R. B. Horsch, A. Matzke, M. D. Chilton, W. S. Chilton and P. R. Sanders (1984) *Plant Molecular Biology* 3, 371–378.
A. Frank., H. Guilley, G. Joward, K. Richards and L. Hirth (1980) *Cell* 21, 285–294.
R. C. Gardner et al, *Nucleic Acids Research* Vol. 9 No. 12: 287 (1981)
G. Guilley et al, *Cell* 30: 763 (1982)
T. Hohn et al, in Gene Cloning in Organisms Other than *E. coli*, p. 193, Hofschneider and Goebel, eds. (Springer Verlag, N.Y., 1982)
A. S. Howarth et al, *Virology* 112:678 (1981)
T. Maniatis et al, Molecular Cloning—A Laboratory Manual (Cold Spring Harbor, Lab, 1982)
R. E. F. Matthews (ed.) *Plant Virology* (Academic Press, N.Y., 1970).
R. C. Mulligan et al, *Nature* 277: 108 (1979).
R. N. Rao and S. Rogers, *Gene* 7: 79 (1979).
S. Rogers et al., (1985) *Plant Mol. Rep.* 3:111.
P. J. Southern & P. Berg, *J. Mol. Appl. Gen.* 1 327 (1982).
L. Stryer, *Biochemistry*, 2nd. ed. (Freeman and Co. San Francisco, 1981).
M. Zoller et al., (1982) *Nucleic Acids Res.* 10:6487.

We claim:

1. A chimeric gene which is expressed in plant cells comprising a promoter from a cauliflower mosaic virus, said promoter selected from the group consisting of a CaMV (35S) promoter isolated from CaMV protein-encoding DNA sequences and a CaMV (19S) promoter isolated from CaMV protein-encoding DNA sequences, and a structural sequence which is heterologous with respect to the promoter.

2. A chimeric gene of claim 1 in which the promoter is the CaMV(35S) promoter.

3. A chimeric gene of claim 1 in which the promoter is the CaMV(19S) promoter.

4. A plant cell which comprises a chimeric gene that contains a promoter from cauliflower mosaic virus, said promoter selected from the group consisting of a CaMV (35S) promoter and a CaMV (19S) promoter, wherein said promoter is isolated from CaMV protein-encoding DNA sequences, and a structural sequence which is heterologous with respect to the promoter.

5. A plant cell of claim 4 in which the promoter is the CaMV(35S) promoter.

6. A plant cell of claim 4 in which the promoter is the CaMV(19S) promoter.

7. An intermediate plant transformation plasmid which comprises a region of homology to an *Agrobacterium tumefaciens* vector, a T-DNA border region from *Agrobacterium tumefaciens* and a chimeric gene, wherein the chimeric gene is located between the T-DNA border and the region of homology, said chimeric gene comprising a promoter from cauliflower mosaic virus, said promoter selected from the group consisting of a CaMV(35S) promoter and a CaMV(19S) promoter, and a structural sequence which is heterologous with respect to the promoter.

8. A plant transformation vector which comprises a disarmed plant tumor inducing plasmid of *Agrobacterium tumefaciens* and a chimeric gene, wherein the chimeric gene contains a promoter from cauliflower mosaic virus, said promoter selected from the group consisting of a CaMV(35S) promoter and a CaMV(19S) promoter, and a structural sequence which is heterologous with respect to the promoter.

9. A plant transformation vector of claim 8 in which the promoter is the CaMV(35S) promoter.

10. A plant transformation vector of claim 8 in which the promoter is the CaMV(19S) promoter.

11. The chimeric gene of claim 1 comprising in the 5' to 3' direction:
 (1) the CaMV(35S) promoter,
 (2) a structural sequence encoding neomycin phosphotransferase II, and
 (3) a 3' non-translated polyadenylation sequence of nopaline synthase.

12. The chimeric gene of claim 1 comprising in the 5' to 3' direction:
 (1) the CaMV(19S) promoter,
 (2) a structural sequence encoding neomycin phosphotransferase II, and
 (3) a 3' non-translated polyadenylation sequence of nopaline synthase.

13. A DNA construct comprising:
 (A) a CaMV promoter selected from the group consisting of (1) a CaMV 35S promoter isolated from CaMV protein-encoding DNA sequences and (2) a CaMV 19S promoter isolated from CaMV protein-encoding DNA sequences, and
 (B) a DNA sequence of interest heterologous to (A), wherein (B) is under the regulatory control of (A) when said construct is transcribed in a plant cell.

14. A chimeric gene which is transcribed and translated in plant cells, said chimeric gene comprising a promoter from cauliflower mosaic virus, said promoter selected from the group consisting of:
 a) a CaMV 35S promoter region free of CaMV protein-encoding DNA sequences and
 b) a CaMV 19S promoter region free of CaMV protein-encoding DNA sequences,
and a DNA sequence which is heterologous with respect to the promoter.

15. A chimeric gene which is expressed in plants cells comprising a promoter from a cauliflower mosaic virus, said promoter selected from the group consisting of a CaMV(35S) promoter region free of CaMV protein-encoding DNA sequences and a CaMV(19S) promoter region free of CaMV protein-encoding DNA sequences, and a DNA sequence which is heterologous with respect to the promoter.

16. A chimeric gene which is transcribed in plants cells comprising a promoter from a cauliflower mosaic virus, said promoter selected from the group consisting of a CaMV(35S) promoter free of CaMV protein-encoding DNA sequences and a CaMV(19S) promoter free of CaMV protein-encoding DNA sequences, a DNA sequence which is heterologous with respect to the promoter and a 3' non-translated polyadenylation signal sequence.

17. A plant cell which comprises a chimeric gene where said chimeric gene comprises a promoter from cauliflower mosaic virus, said promoter selected from the group consisting of a CaMV(35S) promoter and a CaMV(19S) promoter, wherein said promoter is free of CaMV protein-encoding DNA sequences, and a DNA sequence which is heterologous with respect to the promoter and a 3' non-translated polyadenylation signal sequence.

18. An intermediate plasmid of claim 7 in which the promoter is the CaMV(19S) promoter.

19. An intermediate plasmid of claim 7 in which the promoter is the CaMV(35S) promoter.

* * * * *

(12) EX PARTE REEXAMINATION CERTIFICATE (6137th)
United States Patent
Fraley et al.

(10) Number: US 5,352,605 C1
(45) Certificate Issued: Mar. 4, 2008

(54) CHIMERIC GENES FOR TRANSFORMING PLANT CELLS USING VIRAL PROMOTERS

(75) Inventors: Robert T. Fraley, Ballwin, MO (US); Robert B. Horsch, St. Louis, MO (US); Stephen G. Rogers, St. Louis, MO (US)

(73) Assignee: Monsanto Technology LLC, St. Louis, MO (US)

Reexamination Request:
No. 90/008,253, Sep. 29, 2006

Reexamination Certificate for:
Patent No.: 5,352,605
Issued: Oct. 4, 1994
Appl. No.: 08/146,621
Filed: Oct. 28, 1993

Related U.S. Application Data

(63) Continuation of application No. 07/625,637, filed on Dec. 7, 1990, now abandoned, which is a continuation of application No. 06/931,492, filed on Nov. 17, 1986, now abandoned, which is a continuation-in-part of application No. 06/485,568, filed on Apr. 15, 1983, now abandoned, which is a continuation-in-part of application No. 06/458,414, filed on Jan. 17, 1983, now abandoned.

(51) Int. Cl.
*C07K 14/435* (2006.01)
*C07K 14/61* (2006.01)
*C12N 15/82* (2006.01)
*C12N 15/52* (2006.01)

(52) U.S. Cl. .................. 435/418; 435/320.1; 536/23.2; 536/24.1

(58) Field of Classification Search ...................... None
See application file for complete search history.

(56) References Cited

U.S. PATENT DOCUMENTS

| | | | |
|---|---|---|---|
| 4,237,224 A | 12/1980 | Cohen et al. | |
| 4,351,130 A | 9/1982 | Rutger et al. | |
| 4,377,921 A | 3/1983 | Mehra-Palta et al. | |
| 4,378,655 A | 4/1983 | Johnson | |
| 4,407,956 A | 10/1983 | Howell | |
| 4,769,061 A | 9/1988 | Comai | |
| 5,106,739 A | 4/1992 | Comai et al. | |
| 6,174,724 B1 * | 1/2001 | Rogers et al. | 435/419 |

FOREIGN PATENT DOCUMENTS

| | | |
|---|---|---|
| EP | 0 027 662 A1 | 4/1981 |
| EP | 0 067 553 A2 | 12/1982 |
| EP | 093 6129 B1 | 11/1983 |
| EP | 0 115 673 B1 | 8/1984 |
| EP | 0 131 620 | 8/1984 |
| EP | 0 122 791 B2 | 10/1984 |
| EP | 0 148 605 B2 | 7/1985 |
| EP | 0 193 259 B1 | 9/1986 |
| EP | 0 290 799 A2 | 11/1988 |
| EP | 0 339 009 B1 | 10/1989 |
| EP | 0 131 623 B2 | 7/1999 |
| FR | 2500847 | 3/1982 |
| WO | WO 83 01176 | 4/1983 |

OTHER PUBLICATIONS

Hohn et al (Current Topics in Microbiology and Immunology, vol. 96, pp. 193–236, 1982).*

Ammerer, et al., Recombinant DNA, *Proceedings of the Third Cleveland Symposium on Macromolecules* (A.G. Walton, ed.), Jun. 1981, pp. 185–197.

Caplan, A., et al., Introduction of genetic material into plant cells, *Science* 222:815–821 (1983).

Chen, Chang–jie, et al., Internal duplication and homology with bacterial transport proteins in the mdr1 (P–glycoprotein) gene from multidrug–resistant human cells, *Cell* 47:381–389 (1986).

Clements, J. Barklie, et al., Temporal regulation of herpes simplex virus type 1 transcription: location of transcripts on the viral genome, *Cell* 12:275–285 (1977).

Ditta, Gary, et al., Broad host range DNA cloning system for gram–negative bacteria: construction of a gene bank of Rhizobium meliloti, *Proceedings of the National Academy of Sciences USA* 77(12):7347–7351 (1980).

Fling, Mary E., et al., Nucleotide sequence of the transposon Tn7 gene encoding an aminoglyoside–modifying enzyme, 3″(9)–O–nucleotidyltransferase, *Nucleic Acids Research* 13(19):7095–7106 (1985).

Fraley, Robert T., et al., The SEV system: a new disarmed Ti plasmid vector system for plant transformation, *Bio/Technology* 3:629–635 (1985).

Green, Maurice, et al., Autonomous functional domains of chemically synthesized human immunodeficiency virus tat trans–activator protein, *Cell* 55(6):1179–1188 (1988).

Horsch, R.B., et al., A simple and general method for transferring genes into plants, *Science* 277:1229–1231 (1985).

Koncz, Casaba, et al., The promoter of TL–DNA gene 5 controls the tissue–specific expression of chimeric genes carried by novel type of Agrobacterium binary vector, *Molecular and General Genetics* 204:383–396 (1986).

Larkin, P.J., et al., abstract presented in the Proceedings of the International Congress of Plant Tissue and Cell Culture, Tokyo, Japan, Jul. 11–16, 1982.

Lorz, H., et al., abstract of "Transformation studies using synthetic DNA vectors coding for antibiotic resistance," presented at International Congress of Plant Tissue and Cell Culture, Tokyo, Japan, Jul. 11–16, 1982.

(Continued)

*Primary Examiner*—Padmashri Ponnaluri

(57) ABSTRACT

In one aspect the present invention relates to the use of viral promoters in the expression of chimeric genes in plant cells. In another aspect this invention relates to chimeric genes which are capable of being expressed in plant cells, which utilize promoter regions derived from viruses which are capable of infecting plant cells. One such virus comprises the cauliflower mosaic virus (CaMV). Two different promoter regions have been derived from the CaMV genome and ligated to heterologous coding sequences to form chimeric genes. These chimeric genes have been shown to be expressed in plant cells. This invention also relates to plant cells, plant tissue, and differentiated plants which contain and express the chimeric genes of this invention.

OTHER PUBLICATIONS

International Search Report, PCT Application No. US 84/00048, dated Apr. 16, 1984.
Partial European Search Report, EP 84 900 782 application, dated Aug. 28, 1986.
Supplementary European Search Report, EP 84 900 782 application, dated Sep. 2, 1987.
Charles D. Gasser Declaration, dated Apr. 4, 1988 (with attached letter to EPO dated Feb. 4, 1997).
Thomas Hohn Declaration, dated Nov. 12, 1993.
Robert B. Horsch Declaration, dated Dec. 7, 1990.
Robert B. Horsch Declaration, dated Jun. 25, 1993.
Robert B. Horsch Declaration, Jan. 29, 1997.
Harry J. Klee Declaration, dated Jun. 15, 1990.
Dr. Jan Leemans Declaration, dated Oct. 6, 1993.
Joachim Messing Declaration, dated Mar. 29, 1996.
Stephen G. Rogers Declaration, dated Dec. 12, 1989.
Stephen Rogers Declaration, dated Jan. 14, 1997.
Decision of Mar. 7, 1997 in connection with the appeal regarding EP 0 131 623 (Application No. 84/9007828.8), by the Boards of Appeal of the European Patent Office.
Baughman, Gail and Stephen H. Howell, Cauliflower mosaic virus 35 S RNA leader region inhibits translation of downstream genes, Virology 167:125 135 (1988).
Fütterer, Johannes, et al., Differential inhibition of downstream gene expression by the cauliflower mosaic virus 35S RNA leader, *Virus Genes* 3(1):45–55 (1989).
Howarth, Alan J., et al., Nucleotide sequence of naturally occurring deletion mutants of cauliflower mosaic virus, *Virology* 112(2):678–685 (1981).
Howell, Stephen H., The molecular biology of plant DNA viruses, *CRC Critical Reviews in Plant Sciences* 2(4):287–316 (1985).
Timmermans, Marja C. P., et al., Trans replication and high copy numbers of wheat dwarf virus vectors in maize cells, *Nucleic Acids Research* 20(15):4047–4054 (1992).
Timmermans, Marja C. P., et al., Geminiviruses and their uses as extrachromosomal replicons, *Annual Review of Plant Physiology and Plant Molecular Biology* 45:79–112 (1994).
Guilley et al., "Transcription of Cauliflower Mosaic Virus DNA: Detection of Promoter Sequences, and Characterization of Transcripts," Cell, 30(3): 763–773 (1982).
Sequence listing, "*Agrobacterium tumefaciens* pTiT37 T–DNA tmr locus," Gen. Bank Accession No. X00639; Gi 944822.
Comai, Luca, et al., An altered aroA product confers resistance to the herbicide glyphosate, *Science* 221:370–371 (1983).
Comai, Luca, et al., Expression in plants of a mutant aroA gene from *Salmonella typhimurium* confers tolerance to glyphosate, *Nature* 317:741–744 (1985).
Begley, Sharon, et al., "Gene splicing on the farm," *Newsweek*, Aug. 10, 1981, pp. 54–55.
Collection of abstracts on transgenic vascular plants and nopaline synthase or cauliflower mosaic virus from 1983 to present.
Sharp, W.R., et al., Getting out of the wood?, *Cell* 19:303–307 (1980).
Shaw, Charles H., et al., A general method for the transfer of cloned genes to plants, *Gene* 23(3):315–330 (1983).
Shewmaker, C.K., et al., Transcription of cauliflower mosaic virus integrated into plant genomes, *Virology* 140(2):281–288 (1985).

Sieg, K., et al., "Introduction and propagation of foreign DNA in plants using cauliflower mosaic virus as vector," presented at *NATO Advanced Studies Institute/Federation of European Biological Societies Advanced Course: Structure and Function of Plant Genomes*, Porto Portese, Italy, Aug. 23, 1982–Sep. 2, 1982, p. 154 [abstract].
Southern, P.J., et al., Transformation of mammalian cells to antibiotic resistance with a bacterial gene under control of the SV40 early region promoter, *Journal of Molecular and Applied Genetics* 1(4):327–341 (1982).
Stanley, John, et al., Nucleotide sequence of cassava latent virus DNA, *Nature* 301:260–262 (1983).
Stefanov, Ivan., et al., Differential activity of the mannopine synthase and the CaMV 35S promoters during development of transgenic rapeseed plants, *Plant Science* 95(2):175–186 (1994).
Sun, S.M., et al., Intervening sequences in a plant gene—comparison of the partial sequence of cDNA and genomic DNA of French bean phaseolin, *Nature* 289:37–41 (1981).
Sunter, Garry, et al., Transactivation in a geminivirus: AL2 gene product is needed for coat protein expression, *Virology* 180(1): 416–419 (1991).
Timko, Michael P., et al., "Nuclear genes encoding the constituent polypeptides of the light–harvesting chlorophyll a/b–protein complex from pea," *Plant Molecular Biology* (R.B. Goldberg, ed.), New York: Alan R. Liss, Inc., 1983, pp. 403–412.
Vaeck, Mark, et al., Transgenic plants protected from insect attack, *Nature* 328:33–37 (1987).
Vancanneyt, G., et al., Construction of an intron–containing marker gene: splicing of the intron in transgenic plants and its use in monitoring early events in *Agrobacterium*–mediated plant transformation, *Molecular and General Genetics* 220(2):245–250 (1990).
Velten, J., et al., Isolation of a dual plant promoter fragment from the Ti plasmid of *Agrobacterium tumefaciens, The EMBO Journal* 3(12):2723–2730 (1984).
Velten, J., et al. "$T_R$ genes involved in agropine production," *Molecular Genetics of the Bacteria–Plant Interaction*, Berlin: Springer–Verlag, 1983, pp. 303–312.
Wigler, Michael, et al., Transfer of purified herpes virus thymidine kinase gene to cultured mouse cells, *Cell* 11:223–232 (1977).
Willmitzer, Lothar, et al., Size, location and polarity of T–DNA–encoded transcripts in nopaline crown gall tumors; common transcripts in octopine and nopaline tumors, *Cell* 32:1045–1056 (1983).
Wimpee, Charles F., et al., "Sequence heterogeneity in the RuPB carboxylase small subunit gene family of lemna gibba", *Plant Molecular Biology* (R.B. Goldberg, ed.), New York: Alan R. Liss, Inc., 1983, pp. 391–401.
Meagher, Richard B., et al., "Plant actin is encoded by diverse multigene families," *Advances in Gene Technology: Molecular Genetics of Plants and Animals* (Kathleen Downey, et al., eds.), New York: Academic Press, 1983, pp. 171–187.
Messing, Joachim, et al., "Plant gene structure," *Genetic Engineering of Plants—An Agricultural Perspective* (Tsune Kosuge, et al., eds.), New York: Plenum Press, 1983, pp. 211–227 (presented at conference on genetic engineering of plants, University of California at Davis, Aug. 15–19, 1982).
Definition of "cauliflower mosaic virus," *Lexikon der Biochemie und Molekularbiologie*, Freiburg, Germany: Verlag Horder (publisher), 1991, s. 228.

Odell, Joan T., et al., The identification, mapping, and characterization of mRNA for P66, a cauliflower mosaic virus–coded protein, *Virology* 102 (21):349–359 (1980).

Ow, David W., et al., Functional regions of the cauliflower mosaic virus 35S RNA promoter determined by use of the firefly luciferase gene as a reporter of promoter activity, *Proceedings of the National Academy of Sciences* 84(14):4870–4874 (1987).

Peacock, W.J., et al., "Gene transfer in maize: controlling elements and the alcohol dehydrogenase genes," *Advances in Gene Technology: Molecular Genetics of Plants and Animals* (Kathleen Downey, et al., eds.), New York: Academic Press, 1983, pp. 311–325.

Pfeiffer, Pierre, et al., Cauliflower mosaic virus as a probe for studying gene expresison in plants, *Physiologia Plantarum* 77(4):625–632 (1989).

Pfeiffer, Pierre, et al., Involvement of reverse transcription in the replication of cauliflower mosaic virus: a detailed model and test of some aspects, *Cell* 33:781–789 (1983).

Pittard, James, et al., Distribution and function of genes concerned with aromatic biosynthesis in *Escherichia coli*, *Journal of Bacteriology* 91(4):1494–1508 (1966).

Ritchie, Steven W., et al., "Cell culture and regeneration of transgenic plants," *Transgenic Plants* vol. 1 (Shain–dow Kung, et al., eds.), San Diego, California: Academic Press, 1993, pp. 147–178.

Roberts, Thomas M., et al., A general method for maximizing the expression of a cloned gene, *Proceedings of the National Academy of the Sciences USA* 76(2):760–764 (1979).

Sanger, Margaret, et al., Characteristics of a strong promoter from figwort mosaic virus: comparison with the analogous 35S promoter from cauliflower mosaic virus and the regulated mannopine synthase promoter, *Plant Molecular Biology* 14(3):433–443 (1990).

Schell, Jozef, presented at *Genetic Engineering: Applications to Agriculture Symposium*, Beltsville, Maryland, May 16–19, 1982.

Schell, J., et al., Gene vectors for higher plants, in *Genetic Engineering: Applications to Agriculture* (Beltsville Symposium 7—Lowell D. Owen, ed.), Totowa, New Jersey: Rowman & Allanheld, 1983, pp. 197–213.

Shah, Dilip M., et al., Complete nucleotide sequence of a soybean actin gene, *Proceedings of the National Academy of Sciences USA* 79(4):1022–1026 (1982).

Shah, Dilip M., et al., Engineering herbicide tolerance in transgenic plants, *Science* 233:478–481 (1986).

Shannon, K.P., et al., Detection of aminoglycoside–modifying strains of bacteria, *Antibiotics* 183–198 (1983).

Hu, Nien–Tai, et al., Primary structure of a genomic zein sequence of maize, *The EMBO Journal* 1(11):1337–1342 (1982).

Hull, Roger, et al., Does cauliflower mosaic virus replicate by reverse transcription?, *Trends in Biochemical Sciences* 8(4):119–121 (1983).

Hull, Roger, et al., Replication of cauliflower mosaic virus DNA, *Science Progress, Oxford* 68(271):403–422 (1983).

Hyldig–Nielsen, Jens Jørgen, et al., The primary structures of two leghemoglobin genes from soybean, *Nucleic Acids Research* 10(2):689–701 (1982).

Janssen, Bart–Jan, et al., Localized transient expression of GUS in leaf discs following cocultivation with *Agrobacterium*, *Plant Molecular Biology* 14(1):61–72 (1990).

Kemp, John D., et al., transcript of oral presentation presented at *Genetic Engineering: Applications to Agriculture Symposium*, Beltsville, Maryland, May 16–19, 1982, pp. 215–228.

Koncz, C., et al., A simple method to transfer, integrate and study expression of foreign genes, such as chicken ovalbumin and α–actin in plant tumors, *The EMBO Journal* 3(5):1029–1037 (1984).

Lee, Lisa, et al., "Control of tuber protein synthesis in potato," *Plant Molecular Biology* (R.B. Goldberg, ed.), New York: Alan R. Liss, Inc., 1983, pp. 355–365.

Leemans, Jan, Ti to tomato, tomato to market: a decade of plant biotechnology, *Bio/Technology* 11:522–526 (1993).

Lung, M.C.Y., et al., *Datura stramonium*, a local lesion host for certain isolates of cauliflower mosaic virus, *Phytopathological Notes* 62(12):1473–1475 (1972).

Lurquin, Paul F., Entrapment of plasmid DNA by liposomes and their interactions with plant protoplasts, *Nucleic Acids Research* 6(12):3773–3784 (1979).

Maliga, P., et al., Streptomycin–resistant plants from callus culture of haploid tobacco, *Nature New Biology* 224:29–30 (1973).

Marks, M. David, et al., "Molecular structure and expression of maize zein genes," *Advances in Gene Technology: Molecular Genetics of Plants and Animals* (Kathleen Downey, et al., eds.), New York: Academic Press, 1983, pp. 369–381.

Matthews, R.E.F., "Replication III: other virus groups and families," *Plant Virology* (3d ed.), New York: Academic Press, 1991, pp. 271–280.

Matzke, M.A., et al., Transcription of a zein gene introduced into sunflower using a Ti plasmid vector, *The EMBO Journal* 3(7):1525–1531 (1984).

McKnight, Steven L., et al., Analysis of transcriptional regulatory signals of the HSV thymidine kinase gene: identification of an upstream control region, *Cell* 25:385–398 (1981).

McKnight, Steven L., Functional relationships between transcriptional control signals of the thymidine kinase gene herpes simplex virus, *Cell* 31:355–365 (1982).

Currier, T. C., et al., Evidence for diverse types of large plasmids in tumor–inducing strains of *Agrobacterium*, *Journal of Bacteriology* 126(1):157–165 (1976).

DeGreve, Henri, et al., Regeneration of normal and fertile plants that express octopine synthase, from tobacco crown galls after deletion of tumour–controlling functions, *Nature* 300:752–755 (1982).

Dudley, R. Keith, et al., Structure and 5'–termini of the large and 19 S RNA transcripts encoded by the cauliflower mosaic virus genome, *Virology* 117:19–28 (1982).

Ebert, Paul R., et al., Identification of an essential upstream element in the nopaline synthase promoter by stable and transient assays, *Proceedings of the National Academy of Sciences* 84(16):5745–5749 (1987).

Fenoll, Carmen, et al., The intergenic region of maize streak virus contains promoter elements involved in rightward transcription of the viral genome, *The EMBO Journal* 7(6):1589–1596 (1988).

Fraley, Robert T., et al., Use of a chimeric gene to confer antibiotic resistance to plant cells, *Chemical Abstracts* 101 (23):205249p, at p. 149 (1984).

Flavell, Richard B., et al., Selectable marker genes: safe for plants?, *Bio/Technology* 10(2):141–144 (1992).

Fling, Mary E., et al., Protein expression in *Escherichia coli* minicells containing recombinant plasmids specifying trimethoprim–resistant dihydrofolate reductases, *Journal of Bacteriology* 141(2):779–785 (1980).

Fraley, Robert and Demetrios Papahadjopoulos, "Liposomes—the development of a new carrier system for introducing nucleic acids into plant and animal cells," *Gene Cloning In Organisms Other Than E. coli*, Berlin: Springer–Verlag, 1982, pp. 171–191.

Gardner, Richard C., et al., The complete nucleotide sequence of an infectious clone of cauliflower mosaic virus by M13mp7 shotgun sequencing, *Nucleic Acids Research* 9(12):2871–2888 (1981).

Geraghty, Dan, et al., The primary structure of a plant storage protein: zein, *Nucleic Acids Research* 9(19):5163–5174 (1981).

Gerlach, W.L., et al., cDNA cloning and induction of the alcohol dehydrogenase gene (Adhl) of maize, *Proceedings of the National Academy of Sciences* 79(9):2981–2985 (1982).

Gordon, Milton P., et al., "Current developments in the transformation of plants," *Advances in Gene Technology: Molecular Genetics of Plants and Animals* (Kathleen Downey, et al., eds.), New York: Academic Press, 1983, pp. 37–46.

Hall, Timothy C., "The phaseolin family of seed protein genes: sequences and properties," *Advances in Gene Technology: Molecular Genetics of Plants and Animals* (Kathleen Downey, et al., eds.), New York: Academic Press, 1983, pp. 349–367.

Hall, Timothy C., "Workshop summary: from test tube to farm," *Plant Molecular Biology* (R.B. Goldberg, ed.), New York: Alan R. Liss, Inc., 1983, pp. 481–484.

Herrera–Estrella, Luis and J. Simpson, "Gene expression analysis in transgenic plants," *Plant Molecular Biology: A Practical Approach* (C.H. Shaw, ed.), Oxford, England: IRL Press, 1988, pp. 146–149.

Howarth, Alan J., et al., Plant viruses with genomes of single–stranded DNA, *Trends in Biochemical Science* 7:180–182 (1982).

Jaynes, Jesse M., et al., "The position of *Agrobacterium rhizogenes*," *International Review of Cytology Suppl 13—Biology of the Rhizobiaceae* (G. H. Bourne, et al., eds.), New York: Academic Press, 1981, pp. 105–125.

Kellogg, S.T., et al., Plasmid–assisted molecular breeding: new technique for enhanced biodegradation of persistent toxic chemicals, *Science* 214:1133–1135 (1981).

Ream, Lloyd W., et al., Crown gall disease and prospects for genetic manipulation of plants, *Science* 218:854–859 (1982).

An, Gynheung, Development of plant promoter expression vectors and their use for analysis of differential activity of nopaline synthase promoter in transformed tobacco cells, *Plant Physiology* 81:86–91 (1986).

Banerji, Julian, et al., Expression of a β–globin gene is enhanced by remote SV40 DNA sequences, *Cell* 27:299–308 (1981).

Beachy, R.N., et al., Accumulation and assembly of soybean β–conglycinin in seeds of transformed petunia plants, *The EMBO Journal* 4(12):3047–3053 (1985).

Beachy, Roger N., et al., "Molecular characterization of a soybean variety lacking a subunit of the 7S seed storage protein," *Plant Molecular Biology* (R.B. Goldberg, ed.), New York: Alan R. Liss, Inc., 1983, pp. 413–422.

Bedbrook, John R., et al., Molecular cloning and sequencing of cDNA encoding the precursor to the small subunit of chloroplast ribulose–1,5–bisphosphate carboxylase, *Nature* 287:692–697 (1980).

Berk, Arnold J., Adenovirus promoters and E1A transactivation, *Annual Review of Genetics* 20:45–79 (1986).

Berk, Arnold J., et al., Sizing and mapping of early adenovirus mRNAs by gel electrophoresis of S1 endonuclease–digested hybrids, *Cell* 12:721–732 (1977).

Broglie, Richard, et al., Light–regulated expression of a pea ribulose–1,5–biphosphate carboxylase small subunit gene in transformed plant cells, *Science* 224:838–843 (1984).

Broglie, Richard, et al., Structural analysis of nuclear genes coding for the precursor to the small subunit of wheat ribulose–1,5–bisphosphate carboxylase, *Bio/Technology* 1:55–61 (1983).

Chen, Irvin S.Y., Regulation of AIDS virus expression, *Cell* 47(1):1–2 (1986).

Cocking, E.C., et al., Aspects of plant genetic manipulation, *Nature* 293:265–270 (1981).

Corden, J., et al., Promoter sequences in eukaryotic protein–coding genes, *Science* 209:1406–1414 (1980).

Covey, Simon N., et al., Transcription of cauliflower mosaic virus DNA; detection of transcripts, properties, and location of the gene encoding the virus inclusion body protein, *Virology* 111(2):463–474 (1981).

Craig, Nancy L., et al., "Transposition and site–specific recombination," *Escherichia Coli And Salmonella Typhimurium: Cellular And Molecular Biology* (Frederick C. Neidhardt, et al., eds.), Washington, D.C.: American Society for Microbiology, 1987, pp. 1054–1070.

Boshart, Michael, et al., A very strong enhancer is located upstream of an immediate early gene of hyman cytomegalovirus, *Cell* 41:521–530 (1985).

Dennis, Elizabeth, et al., Transcription from a plant gene promoter in animal cells, *Nucleic Acids Research* 13(22):7945–7957 (1985).

Hunt, Arthur G., et al., Plant cells do not properly recognize animal gene polyadenylation signals, *Plant Molecular Biology* 8(1):23–35 (1987).

Kay, Robert, et al., Duplication of CaMV 35S promoter sequences creates a strong enhancer for plant genes, *Science* 236:1299–1302 (1987).

Khoury, George, et al., Enhancer elements, *Cell* 33(2):313–314 (1983).

Kumar, Ramesh, et al., Activation of gene expression is adversely affected at high multiplicities of linked simian virus 40 enhancer, *Proceedings of the National Academy of Sciences* 83(1):3199–3203 (1986).

Odell, Joan T., et al., Properties of an isolated transcription stimulating sequence derived from the cauliflower mosaic virus 35S promoter, *Plant Molecular Biology* 10(3):263–272 (1988).

Rogers, S.G., et al., Improved vectors for plant transformation: expression cassette vectors and new selectable markers, *Methods in Enzymology* vol. 153, San Diego, California: Academic Press, 1987, pp. 253–277.

Sanders, P. R., et al., Comparison of cauliflower mosaic virus 35S and nopaline synthase promoters in transgenic plants, *Nucleic Acids Research* 15(4):1543–1558 (1987).

Schaffner, W., et al., *Eukaryotic transcription: The role of cis– and trans–acting elements in initiation* (Y. Gluzman, ed.), Cold Spring Harbor, New York: Cold Spring Harbor Laboratory (1985), pp. 1–18.

Zenke, Martin, et al., Multiple sequence motifs are involved in SV40 enhancer function, *The EMBO Journal* 5(2):387–397 (1986).

Herrera–Estrella, Luis, et al., Expression of chimaeric genes transferred into plant cells using a Ti–plasmid–derived vector, *Chemical Abstracts* 99(3):17349n (1983).

Kemp, John D., et al., abstract #1159 "Ti plasmid as a vehicle for genetic engineering of plant cells," *Journal of Cellular Biochemistry—12th Annual UCLA Symposia Abstracts (Jan. 30–Apr. 2, 1983)*, suppl. 7A, New York: Alan R. Liss, Inc., 1983, p. 245.

Barton, Kenneth A., et al., Prospects in plant genetic engineering, *Science* 219:671–676 (1983).

Carlson, P.S., Genetic engineering in plants retrospect and prospects, *Biological Abstracts/RRM*, ref. No. 25045990, Philadelphia; and *Abstr. Pap. Am. Chem. Soc.* vol. 193 (1982) pPEST–59.

Choudary, Prabhakara V., et al., "Studies on expression of the phaseolin gene of French bean seeds in sunflower plant cells," presented at *From Gene To Protein, Translation In Biotechnology (Miami Winter Symposia* vol. 19) (F. Ahmad, et al., eds.), New York: Academic Press, 1982, p. 514 [abstract].

Comai, Luca, et al., A new technique for genetic engineering of *Agrobacterium* Ti plasmid, *Plasmid* 10:21–30 (1983).

Luria, Salvador E., et al., *General Virology* (3d ed), New Jersey: John Wiley & Sons, Inc., 1978.

Marx, Jean L., Ti plasmids as gene carriers—when suitably modified, tumor–inducing plasmids can transfer genes into plant cells from which normal plants may be regenerated, *Science* 216:1305 (1982).

Murai, Norimoto, et al., Phaseolin gene from bean is expressed after transfer to sunflower via tumor–inducing plasmid vectors, *Science* 222:476–482 (1983).

Odell, Joan T., et al., Identification of DNA sequences required for activity of the cauliflower mosaic virus 35S promoter, *Nature* 313:810–812 (1985).

Odell, Joan T., et al., Structure of the 19 S RNA transcript encoded by the cauliflower mosaic virus genome, *Virology* 111(2):377–385 (1981).

Old, R.W., et al., *Principles of Genetic Engineering—An Introduction To Genetic Engineering* (1st ed.), Oxford, England: Blackwell Scientific Publications, 1980, p. 22.

Seeburg, P.H., et al., Efficient bacterial expression of bovine and porcine growth hormones, *DNA* 2(1):37–45 (1983).

Stalker, David M., et al., Nucleotide sequence of the region of the origin of replication of the broad host range plasmid RK2, *Molecular and General Genetics* 181(1):8–12 (1981).

Studier, F. William, Bacteriophage T7: genetic and biochemical analysis of this simple phage gives information about basic genetic processes, *Science* 176(33):367–376 (1972).

Thomas, Kirk R., et al., Site–directed mutagenesis by gene targeting in mouse embryo–derived stem cells, *Cell* 51:503–512 (1987).

Travers, Andrew A. and Richard R. Burgess, Cyclic re–use of the RNA polymerase sigma factor, *Nature* 222:537–540 (1969).

Tuite, M.F., et al., Regulated high efficiency expression of human interferon–alpha in *Saccharomyces cerevisiae*, *The EMBO Journal* 1(5):603–608 (1982).

Barker, R.F., et al., Nucleotide sequence of the T–DNA region from the *Agrobacterium tumefaciens* octopine Ti plasmid pTi15955, *Plant Molecular Biology* 2(6):335–350 (1983).

Barton, Kenneth A., et al., Regeneration of intact tobacco plants containing full length copies of genetically engineered T–DNA, and transmission of T–DNA to R1 progeny, *Cell* 32(4):1033–1043 (1983).

Howell, Stephen H., et al., Rescue of in vitro generated mutants of cloned cauliflower mosaic virus genomie in infected plants, *Nature* 293:483–486 (1981).

Kim, Younghee, et al., A 20 nucleotide upstream element is essential for the nopaline synthase (nos) promoter activity, *Plant Molecular Biology* 24(1):105–117 (1994).

Lippincott, James A., et al., Cell walls to crown–gall tumors and embryonic plant tissues lack *Agrobacterium* adherence sites, *Science* 199:1075–1078 (1978).

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–19 is confirmed.

New claims 20–67 are added and determined to be patentable.

20. *A chimeric gene comprising a promoter from a cauliflower mosaic virus, said promoter selected from the group consisting of a CaMV(35S) promoter free of CaMV protein-encoding DNA sequences and a CaMV(19S) promoter free of CaMV protein-encoding DNA sequences, a structural DNA sequence which is heterologous with respect to the promoter and a 3' non-translated polyadenylation signal sequence, wherein the structural DNA sequence is under the regulatory control of the promoter and wherein said chimeric gene is transcribed in a plant cell.*

21. *The chimeric gene of claim 20 in which the promoter is the CaMV(35S) promoter.*

22. *The chimeric gene of claim 20 in which the promoter is the CaMV(19S) promoter.*

23. *The chimeric gene of claim 21, wherein the promoter comprises a 330 base pair EcoRI-BglII fragment of pMON273.*

24. *The chimeric gene of claim 21, wherein the promoter comprises a 330 base pair fragment from nucleotide 7143 to nucleotide 7517 of the CaMV genome.*

25. *The chimeric gene of claim 22, wherein the promoter comprises a 400 base pair HindIII-XbaI fragment of pMON203.*

26. *A chimeric gene comprising a promoter from a cauliflower mosaic virus, said promoter selected from the group consisting of a CaMV(35S) promoter free of CaMV protein-encoding DNA sequences and a CaMV(19S) promoter free of CaMV protein-encoding DNA sequences, a structural DNA sequence which is heterologous with respect to the promoter and a 3' non-translated polyadenylation signal sequence, wherein the structural DNA sequence is under the regulatory control of the promoter and wherein said chimeric gene is expressed in a plant cell.*

27. *The chimeric gene of claim 26 in which the promoter is the CaMV(35S) promoter.*

28. *The chimeric gene of claim 26 in which the promoter is the CaMV(19S) promoter.*

29. *The chimeric gene of claim 27, wherein the promoter comprises a 330 base pair EcoRI-BglII fragment of pMON273.*

30. *The chimeric gene of claim 27, wherein the promoter comprises a 330 base pair fragment from nucleotide 7143 to nucleotide 7517 of the CaMV genome.*

31. *The chimeric gene of claim 28, wherein the promoter comprises a 400 base pair HindIII-XbaI fragment of pMON203.*

32. *A genetically transformed plant cell which comprises a chimeric gene where said chimeric gene comprises a promoter from cauliflower mosaic virus, said promoter selected from the group consisting of a CaMV(35S) promoter and a CaMV(19S) promoter, wherein said promoter is free of CaMV protein-encoding DNA sequences, and a structural DNA sequence which is heterologous with respect to the promoter and a 3' non-translated polyadenylation signal sequence, wherein the structural DNA sequence is under the regulatory control of the promoter and wherein said chimeric gene is incorporated into the nuclear genome of the plant cell.*

33. *The genetically transformed plant cell of claim 32 in which the promoter is the CaMV(35S) promoter.*

34. *The genetically transformed plant cell of claim 32 in which the promoter is the CaMV(19S) promoter.*

35. *The genetically transformed plant cell of claim 33, wherein the promoter comprises a 330 base pair EcoRI-BglII fragment of pMON273.*

36. *The genetically transformed plant cell of claim 33, wherein the promoter comprises a 330 base pair fragment from nucleotide 7143 to nucleotide 7517 of the CaMV genome.*

37. *The genetically transformed plant cell of claim 34, wherein the promoter comprises a 400 base pair HindIII-XbaI fragment of pMON203.*

38. *A plant cell which comprises the chimeric gene of claim 14.*

39. *A plant cell which comprises the chimeric gene of claim 15.*

40. *The chimeric gene of claim 1 which does not contain any of the CaMV coding sequence translational initiators.*

41. *The plant cell of claim 4 wherein the chimeric gene does not contain any of the CaMV coding sequence translational initiators.*

42. *The DNA construct of claim 13 which does not contain any of the CaMV coding sequence translational initiators.*

43. *The chimeric gene of claim 14 which does not contain any of the CaMV coding sequence translational initiators.*

44. *The chimeric gene of claim 15 which does not contain any of the CaMV coding sequence translational initiators.*

45. *The chimeric gene of claim 16 which does not contain any of the CaMV coding sequence translational initiators.*

46. *The plant cell of claim 17 wherein the chimeric gene does not contain any of the CaMV coding sequence translational initiators.*

47. *The chimeric gene of claim 20 which does not contain any of the CaMV coding sequence translational initiators.*

48. *The chimeric gene of claim 26 which does not contain any of the CaMV coding sequence translational initiators.*

49. *The genetically transformed plant cell of claim 32 wherein the chimeric gene does not contain any of the CaMV coding sequence translational initiators.*

50. *The chimeric gene of claim 2, wherein the promoter comprises a 330 base pair EcoRI-BglII fragment of pMON273.*

51. *The chimeric gene of claim 2, wherein the promoter comprises a 330 base pair fragment from nucleotide 7143 to nucleotide 7517 of the CaMV genome.*

52. *The chimeric gene of claim 3, wherein the promoter comprises a 400 base pair HindIII-XbaI fragment of pMON203.*

53. *The plant cell of claim 5, wherein the promoter comprises a 330 base pair EcoRI-BglII fragment of pMON273.*

54. *The chimeric gene of claim 5, wherein the promoter comprises a 330 base pair fragment from nucleotide 7143 to nucleotide 7517 of the CaMV genome.*

55. *The plant cell of claim 6, wherein the promoter comprises a 400 base pair HindIII-XbaI fragment of pMON203.*

56. A chimeric gene comprising a promoter from a cauliflower mosaic virus selected from the group consisting of a CaMV(35S) promoter and a CaMV(19S) promoter, a structural DNA sequence which is heterologous with respect to the promoter and a 3' non-translated polyadenylation signal sequence, wherein the structural DNA sequence is under the regulatory control of the promoter and wherein said chimeric gene does not encode any complete CaMV protein.

57. The chimeric gene of claim 56 in which the promoter is the CaMV(35S) promoter.

58. The chimeric gene of claim 56 in which the promoter is the CaMV(19S) promoter.

59. The chimeric gene of claim 57, wherein the promoter comprises a 330 base pair EcoRI-BglII fragment of pMON273.

60. The chimeric gene of claim 57, wherein the promoter comprises a 330 base pair fragment from nucleotide 7143 to nucleotide 7517 of the CaMV genome.

61. The chimeric gene of claim 58, wherein the promoter comprises a 400 base pair HindIII-XbaI fragment of pMON203.

62. The genetically transformed plant cell comprising a chimeric gene where said chimeric gene comprises a promoter from a cauliflower mosaic virus selected from the group consisting of a CaMV(35S) promoter and a CaMV(19S) promoter, a structural DNA sequence which is heterologous with respect to the promoter and a 3' non-translated polyadenylation signal sequence, wherein the structural DNA sequence is under the regulatory control of the promoter and wherein said chimeric gene does not encode any complete CaMV protein.

63. The genetically transformed plant cell of claim 62 in which the promoter is the CaMV(35S) promoter.

64. The genetically transformed plant cell of claim 62 in which the promoter is the CaMV(19S) promoter.

65. The genetically transformed plant cell of claim 63, wherein the promoter comprises a 330 base pair EcoRI-BglII fragment of pMON273.

66. The genetically transformed plant cell of claim 63, wherein the promoter comprises a 330 base pair fragment from nucleotide 7143 to nucleotide 7517 of the CaMV genome.

67. The genetically transformed plant cell of claim 64, wherein the promoter comprises a 400 base pair HindIII-XbaI fragment of pMON203.

\* \* \* \* \*